(12) United States Patent
Barrus et al.

(10) Patent No.: US 8,920,471 B2
(45) Date of Patent: Dec. 30, 2014

(54) TRANSVERSE CONNECTOR

(75) Inventors: Michael Barrus, Ashburn, VA (US);
Scott Jones, McMurray, PA (US);
Catherine Ross, Arlington, VA (US)

(73) Assignee: K2M, Inc., Leesburg, VA (US)

( * ) Notice: Subject to any disclaimer, the term of this patent is extended or adjusted under 35 U.S.C. 154(b) by 371 days.

(21) Appl. No.: 13/251,546

(22) Filed: Oct. 3, 2011

(65) Prior Publication Data
US 2012/0035659 A1 Feb. 9, 2012

Related U.S. Application Data

(63) Continuation-in-part of application No. PCT/US2010/041693, filed on Jul. 12, 2010.

(60) Provisional application No. 61/388,642, filed on Oct. 1, 2010.

(51) Int. Cl.
*A61B 17/70* (2006.01)

(52) U.S. Cl.
CPC ......... *A61B 17/7049* (2013.01); *A61B 17/7052* (2013.01)
USPC ............ 606/251; 606/250; 606/252; 606/253

(58) Field of Classification Search
CPC ........... A61B 17/7043; A61B 17/7049; A61B 17/7025; A61B 2017/7073
USPC .................................. 403/114; 606/250–253
See application file for complete search history.

(56) References Cited

U.S. PATENT DOCUMENTS

| | | | |
|---|---|---|---|
| 1,077,052 A * | 10/1913 | Dodds | 411/380 |
| 5,133,716 A | 7/1992 | Plaza | |
| 5,257,994 A | 11/1993 | Lin | |
| 5,261,907 A | 11/1993 | Vignaud et al. | |
| 5,261,911 A | 11/1993 | Carl | |
| 5,275,600 A | 1/1994 | Allard et al. | |
| 5,304,179 A | 4/1994 | Wagner | |
| 5,312,405 A | 5/1994 | Korotko et al. | |
| 5,330,474 A | 7/1994 | Lin | |
| 5,334,203 A | 8/1994 | Wagner | |
| 5,342,361 A | 8/1994 | Yuan et al. | |
| 5,368,594 A | 11/1994 | Martin et al. | |
| 5,374,267 A | 12/1994 | Siegal | |
| 5,380,325 A | 1/1995 | Lahille et al. | |
| 5,382,248 A | 1/1995 | Jacobson et al. | |
| 5,403,316 A | 4/1995 | Ashman | |
| 5,413,576 A | 5/1995 | Rivard | |
| 5,437,669 A | 8/1995 | Yuan et al. | |
| 5,437,671 A | 8/1995 | Lozier et al. | |
| 5,439,463 A | 8/1995 | Lin | |
| 5,466,238 A | 11/1995 | Lin | |
| 5,487,743 A | 1/1996 | Laurain et al. | |
| 5,498,262 A | 3/1996 | Bryan | |
| 5,498,263 A | 3/1996 | DiNello et al. | |
| 5,514,132 A | 5/1996 | Csernátony et al. | |
| 5,522,816 A | 6/1996 | Dinello et al. | |

(Continued)

*Primary Examiner* — Eduardo C Robert
*Assistant Examiner* — Julianna N Harvey
(74) *Attorney, Agent, or Firm* — Carter DeLuca Farrell & Schmidt LLP

(57) ABSTRACT

The present disclosure provides a transverse connector having first and second spinal rod connecting members disposed on opposing ends of a cross member. Each spinal rod connecting member is configured to connect to a spinal rod. The first and second spinal rod connecting members are configured for multidirectional articulation relative to the cross member.

13 Claims, 33 Drawing Sheets

(56) References Cited

U.S. PATENT DOCUMENTS

| | | | |
|---|---|---|---|
| 5,569,246 A | 10/1996 | Ojima et al. |
| 5,582,612 A | 12/1996 | Lin |
| 5,591,167 A | 1/1997 | Laurain et al. |
| 5,601,552 A | 2/1997 | Cotrel |
| 5,601,554 A | 2/1997 | Howland et al. |
| 5,609,592 A | 3/1997 | Brumfield et al. |
| 5,611,800 A | 3/1997 | Davis et al. |
| 5,624,442 A | 4/1997 | Mellinger et al. |
| 5,630,816 A | 5/1997 | Kambin |
| 5,651,789 A | 7/1997 | Cotrel |
| 5,667,506 A | 9/1997 | Sutterlin |
| 5,667,507 A | 9/1997 | Corin et al. |
| 5,669,910 A | 9/1997 | Korhonen et al. |
| 5,688,272 A | 11/1997 | Montague et al. |
| 5,693,053 A | 12/1997 | Estes |
| 5,707,372 A | 1/1998 | Errico et al. |
| 5,709,684 A | 1/1998 | Errico et al. |
| 5,713,900 A | 2/1998 | Benzel et al. |
| 5,716,355 A | 2/1998 | Jackson et al. |
| 5,743,911 A | 4/1998 | Cotrel |
| 5,752,955 A | 5/1998 | Errico |
| 5,810,817 A | 9/1998 | Roussouly et al. |
| 5,843,082 A | 12/1998 | Yuan et al. |
| 5,885,284 A | 3/1999 | Errico et al. |
| 5,947,966 A | 9/1999 | Drewry et al. |
| 5,980,521 A | 11/1999 | Montague et al. |
| 5,980,523 A | 11/1999 | Jackson |
| 5,989,250 A | 11/1999 | Wagner et al. |
| 5,989,251 A | 11/1999 | Nichols |
| 6,050,997 A | 4/2000 | Mullane |
| 6,083,226 A | 7/2000 | Fiz |
| 6,096,039 A | 8/2000 | Stoltenberg et al. |
| 6,106,527 A | 8/2000 | Wu et al. |
| 6,110,173 A | 8/2000 | Thomas, Jr. |
| 6,113,600 A | 9/2000 | Drummond et al. |
| 6,132,430 A | 10/2000 | Wagner |
| 6,136,003 A | 10/2000 | Hoeck et al. |
| 6,139,548 A | 10/2000 | Errico |
| 6,171,311 B1 | 1/2001 | Richelsoph |
| 6,217,578 B1 | 4/2001 | Crozet et al. |
| 6,234,705 B1 | 5/2001 | Troxell |
| 6,238,396 B1 | 5/2001 | Lombardo |
| 6,261,288 B1 | 7/2001 | Jackson |
| 6,264,658 B1 | 7/2001 | Lee et al. |
| 6,283,967 B1 | 9/2001 | Troxell et al. |
| 6,302,882 B1 | 10/2001 | Lin et al. |
| 6,306,137 B2 | 10/2001 | Troxell |
| 6,328,740 B1 | 12/2001 | Richelsoph |
| 6,328,741 B1 | 12/2001 | Richelsoph |
| 6,402,751 B1 | 6/2002 | Hoeck et al. |
| 6,413,258 B1 | 7/2002 | Bernhardt, Jr. |
| 6,432,108 B1 | 8/2002 | Burgess et al. |
| 6,485,491 B1 | 11/2002 | Farris et al. |
| 6,524,310 B1 | 2/2003 | Lombardo et al. |
| 6,554,831 B1 | 4/2003 | Rivard et al. |
| 6,554,832 B2 | 4/2003 | Shluzas |
| 6,565,569 B1 | 5/2003 | Assaker et al. |
| 6,569,164 B1 | 5/2003 | Assaker et al. |
| 6,592,585 B2 | 7/2003 | Lee et al. |
| 6,595,992 B1 | 7/2003 | Wagner et al. |
| 6,602,253 B2 | 8/2003 | Richelsoph et al. |
| 6,613,050 B1 | 9/2003 | Wagner et al. |
| 6,616,668 B2 | 9/2003 | Altarac et al. |
| 6,669,697 B1 | 12/2003 | Pisharodi |
| 6,673,073 B1 | 1/2004 | Schäfer |
| 6,699,248 B2 | 3/2004 | Jackson |
| 6,709,435 B2 | 3/2004 | Lin |
| 6,736,817 B2 | 5/2004 | Troxell et al. |
| 6,749,612 B1 | 6/2004 | Conchy et al. |
| 6,752,807 B2 | 6/2004 | Lin et al. |
| 6,761,721 B2 | 7/2004 | Burgess et al. |
| 6,783,526 B1 | 8/2004 | Lin et al. |
| 6,786,907 B2 | 9/2004 | Lange |
| 6,802,844 B2 | 10/2004 | Ferree |
| 6,866,664 B2 | 3/2005 | Schär et al. |
| 6,872,208 B1 | 3/2005 | McBride et al. |
| 6,875,211 B2 | 4/2005 | Nichols et al. |
| 6,881,215 B2 | 4/2005 | Assaker et al. |
| 6,887,241 B1 | 5/2005 | McBride et al. |
| 6,916,319 B2 | 7/2005 | Munting |
| 6,958,066 B2 | 10/2005 | Richelsoph et al. |
| 6,991,632 B2 | 1/2006 | Ritland |
| 7,008,423 B2 | 3/2006 | Assaker et al. |
| 7,029,472 B1 | 4/2006 | Fortin |
| 7,029,474 B2 | 4/2006 | Richelsoph et al. |
| 7,066,938 B2 | 6/2006 | Slivka et al. |
| 7,104,993 B2 | 9/2006 | Baynham et al. |
| 7,122,036 B2 | 10/2006 | Vanacker |
| 7,137,986 B2 | 11/2006 | Troxell et al. |
| 7,195,632 B2 | 3/2007 | Biedermann et al. |
| 7,220,262 B1 | 5/2007 | Hynes |
| 7,232,441 B2 | 6/2007 | Altarac et al. |
| 7,276,069 B2 | 10/2007 | Biedermann et al. |
| 7,291,152 B2 | 11/2007 | Abdou |
| 7,322,979 B2 | 1/2008 | Crandall et al. |
| 7,335,201 B2 | 2/2008 | Doubler et al. |
| 7,473,269 B1 | 1/2009 | Hynes |
| 7,481,827 B2 | 1/2009 | Ryan et al. |
| 7,485,132 B1 | 2/2009 | McBride et al. |
| 7,530,991 B2 | 5/2009 | Nekozuka et al. |
| 7,569,069 B2 | 8/2009 | Sasing et al. |
| 7,585,314 B2 | 9/2009 | Taylor et al. |
| 7,591,836 B2 | 9/2009 | Dick et al. |
| 7,628,799 B2 | 12/2009 | Richelsoph et al. |
| 7,645,294 B2 | 1/2010 | Kalfas et al. |
| 7,666,210 B2 | 2/2010 | Franck et al. |
| 7,691,129 B2 | 4/2010 | Felix |
| 7,699,872 B2 | 4/2010 | Farris et al. |
| 7,717,938 B2 | 5/2010 | Kim et al. |
| 7,717,939 B2 | 5/2010 | Ludwig et al. |
| 7,717,940 B2 | 5/2010 | Woods et al. |
| 7,722,617 B2 | 5/2010 | Young et al. |
| 7,722,648 B2 | 5/2010 | Drewry et al. |
| 7,736,370 B2 | 6/2010 | Sweeney |
| 7,744,629 B2 | 6/2010 | Hestad et al. |
| 7,744,632 B2 | 6/2010 | Usher |
| 7,744,633 B2 | 6/2010 | Berrevoets et al. |
| 7,758,584 B2 | 7/2010 | Bankoski et al. |
| 7,758,617 B2 | 7/2010 | Iott et al. |
| 7,766,918 B2 | 8/2010 | Allard et al. |
| 7,771,474 B2 | 8/2010 | Cordaro |
| 7,776,075 B2 | 8/2010 | Bruneau et al. |
| 7,776,094 B2 | 8/2010 | McKinley et al. |
| 7,780,704 B2 | 8/2010 | Markworth et al. |
| 7,794,464 B2 | 9/2010 | Bridwell et al. |
| 7,794,478 B2 | 9/2010 | Nilsson |
| 7,799,031 B2 | 9/2010 | Miller et al. |
| 7,806,912 B2 | 10/2010 | Lawton et al. |
| 7,815,666 B2 | 10/2010 | Baynham et al. |
| 2003/0114853 A1* | 6/2003 | Burgess et al. ............... 606/61 |
| 2006/0052785 A1 | 3/2006 | Augostino et al. |
| 2006/0259038 A1 | 11/2006 | Cordaro |
| 2008/0004629 A1 | 1/2008 | Nichols et al. |
| 2008/0009880 A1 | 1/2008 | Warnick et al. |
| 2008/0009881 A1 | 1/2008 | Blatt et al. |
| 2008/0015585 A1 | 1/2008 | Berg et al. |
| 2008/0021459 A1 | 1/2008 | Lim |
| 2008/0306538 A1* | 12/2008 | Moore et al. ............... 606/250 |
| 2010/0057131 A1* | 3/2010 | Ely et al. ............... 606/250 |
| 2010/0094348 A1 | 4/2010 | Biedermann et al. |
| 2010/0094421 A1 | 4/2010 | Mathieu et al. |
| 2010/0106249 A1 | 4/2010 | Tyber et al. |
| 2010/0114173 A1 | 5/2010 | Le Couedic et al. |
| 2010/0114182 A1 | 5/2010 | Wilcox et al. |
| 2010/0137913 A1 | 6/2010 | Khatchadourian et al. |
| 2010/0137915 A1 | 6/2010 | Anderson et al. |
| 2010/0145386 A1 | 6/2010 | Greenhalgh et al. |
| 2010/0145459 A1 | 6/2010 | McDonough et al. |
| 2010/0145460 A1 | 6/2010 | McDonough et al. |
| 2010/0185242 A1 | 7/2010 | Barry et al. |
| 2010/0198261 A1 | 8/2010 | Trieu et al. |
| 2010/0204796 A1 | 8/2010 | Bae et al. |
| 2010/0211105 A1 | 8/2010 | Moumene et al. |
| 2010/0217271 A1 | 8/2010 | Pool et al. |

(56) References Cited

U.S. PATENT DOCUMENTS

| | | |
|---|---|---|
| 2010/0222815 A1 | 9/2010 | Simonson |
| 2010/0228290 A1 | 9/2010 | Courtney et al. |
| 2010/0234895 A1 | 9/2010 | Hess |
| 2010/0241172 A1 | 9/2010 | Biyani et al. |
| 2010/0241231 A1 | 9/2010 | Marino et al. |
| 2010/0249849 A1 | 9/2010 | Sweeney |
| 2010/0249856 A1 | 9/2010 | Iott et al. |
| 2010/0249935 A1 | 9/2010 | Slivka et al. |
| 2010/0262154 A1 | 10/2010 | Evans et al. |
| 2010/0262190 A1 | 10/2010 | Ballard et al. |
| 2010/0262192 A1 | 10/2010 | Foley |

\* cited by examiner

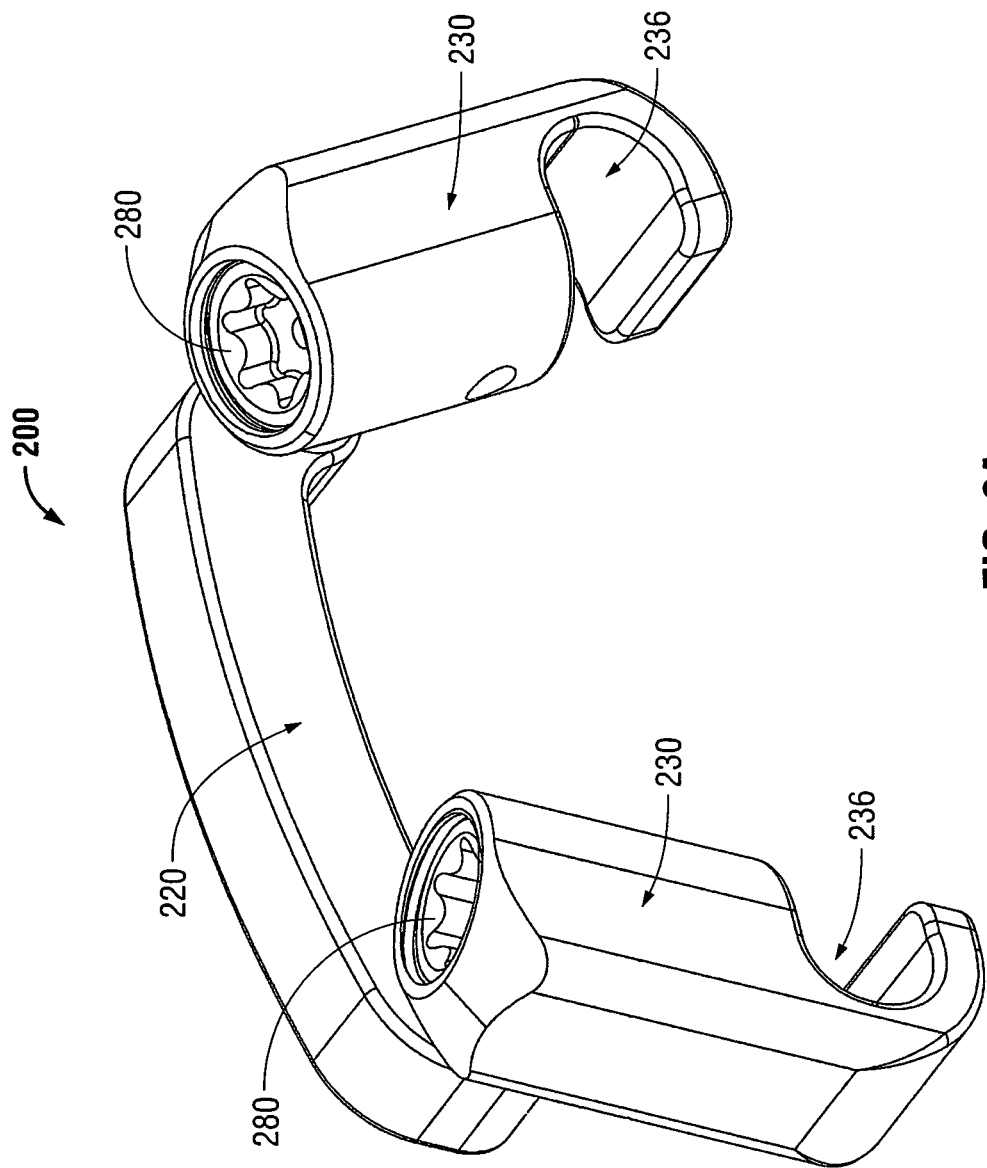

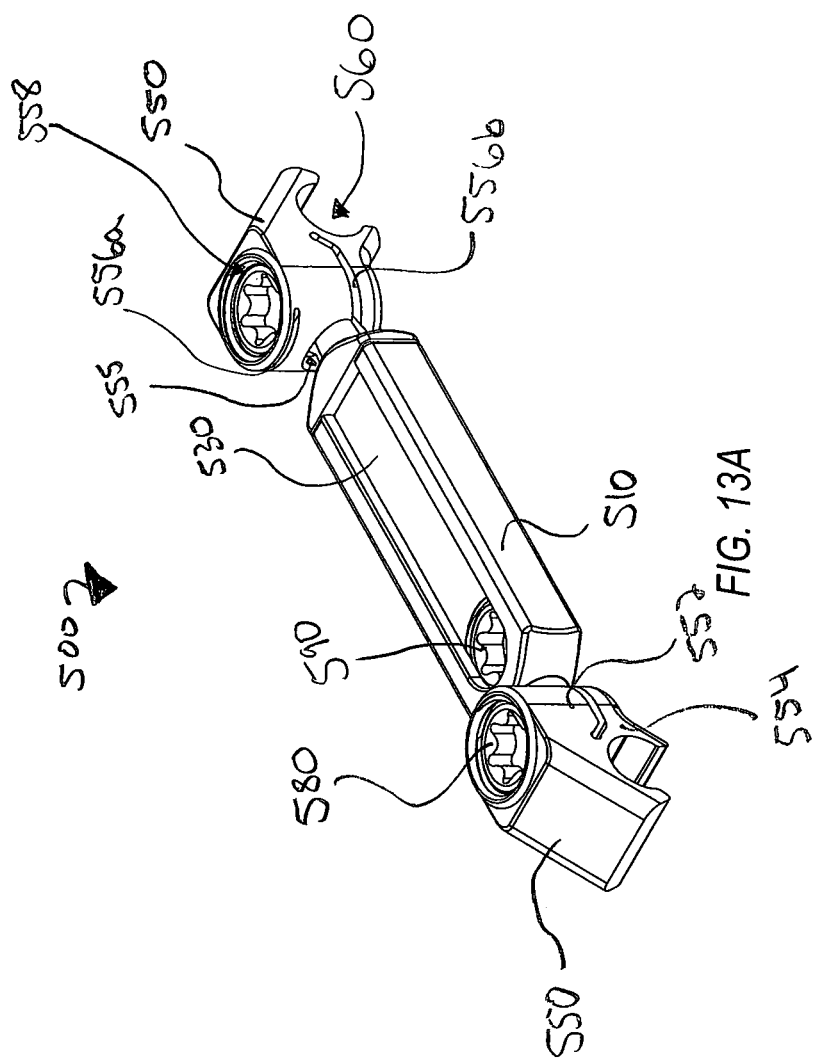

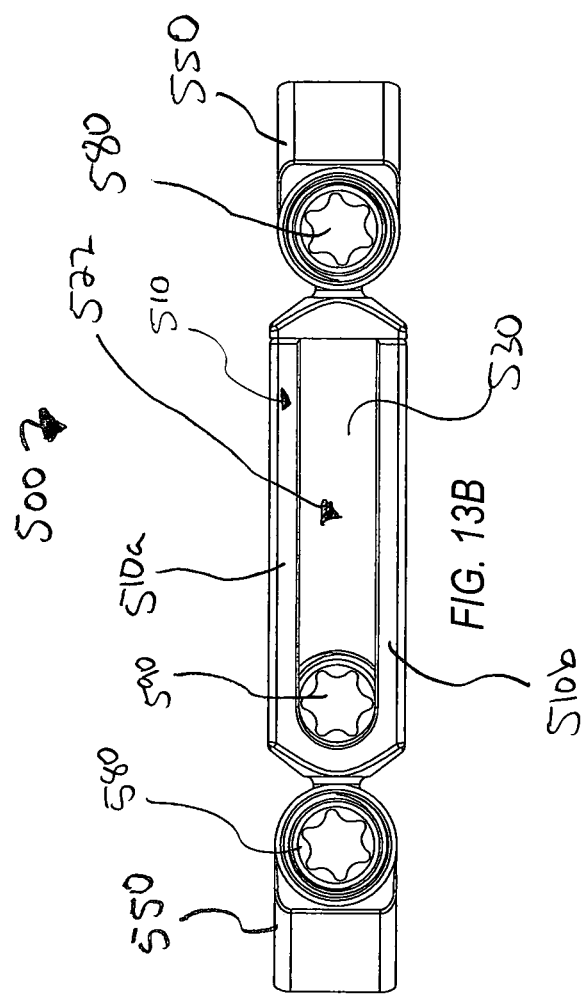

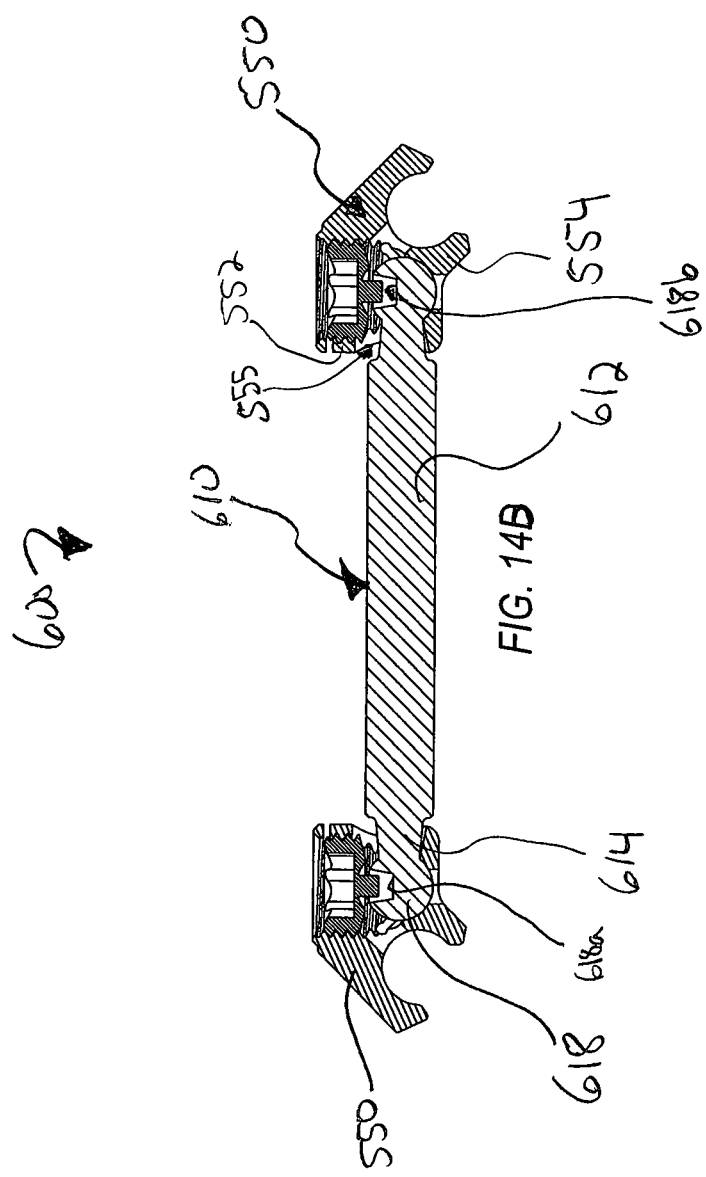

TRANSVERSE CONNECTOR

CROSS-REFERENCE TO RELATED APPLICATIONS

This application is a continuation-in-part of International Application Ser. No. PCT/US2010/041693, filed on Jul. 12, 2010, and claims the benefit of, and priority to, U.S. Provisional Patent Application No. 61/388,642, filed Oct. 1, 2010, the entire contents of each of these prior applications are incorporated by reference.

BACKGROUND

1. Technical Field

The present disclosure relates to a transverse connector for interconnecting a first and a second rod, which are in an approximately parallel relationship to each other. More particularly, the present disclosure relates to an offset transverse connector having opposing ends and being capable of independent multidirectional articulation while preserving space for the anatomy.

2. Background Art

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases. For example, as illustrated in FIG. 16, many of these apparatuses commonly use a pair of longitudinal rods 50 running in a relatively parallel relationship to each other and the spinal column S to correct any spinal deformity involving a convexity or a concavity. These rods 50 are connected to coupling elements, which in turn are secured to the underlying vertebral bone V by spinal bone fixation fasteners such as pedicle screws, hooks, and the like. More particularly, depending upon the nature of the deformity, suitable bone screws 48 may be first implanted into the vertebral bone V of the spinal column S at multiple points above and below the apex A of the curve. Rod reduction devices 10 including manipulation devices 28 adapted and configured for attachment to heads of the bone screws 48, and which provide leverage to facilitate the manipulation of the spinal column S, can then be attached to the heads of the bone screws 48. With continuing reference to FIG. 16, the rod reduction device 10 is attached to the heads of the bone screws 48 on the concave side S1 of the spinal deformity. The manipulator device 28 is placed on the bone screws 48 on the convex side S2 of the spinal deformity. Depending upon the nature of the deformity, the rod reduction device 10 can be used on both sides of the deformity.

Prior to any correction of the rods 50, the surgeon can manipulate and correct the curve of the spinal column S to a large degree. That is, the surgeon can first manually manipulate and reduce the "rib hump." The spinal rod 50 can be pre-bent to the configuration of the normal spinal curve, e.g., the sagittal curve. Once certain the spine S is in the proper anatomical position, the surgeon can position the pre-bent spinal rods 50 relative to the screws 48 and the rod reduction devices 10, and lock each rod 50 to the first two points of the spinal column where the construct is to be attached for enabling the correction of the deformity. In order to facilitate the desired positioning of the pair of longitudinal rods 50 relative to the spinal column S, the pair of longitudinal rods 50 can be held in position relative to one another by transverse connectors, also known as transverse bridge elements or cross-connectors.

As the technology of spinal surgery has developed and improved, each of the spinal fixation components has also undergone improvements and modifications to address the shortcomings of conventional spinal appliances. The natural anatomical variations in the spinal column of a subject are such that implanted spinal rods while approximating a parallel relationship one to the other can vary from that parallel relationship considerably and in multiple planes. For this reason, any transverse connector used to attach the two rods to each other should not be of a rigid design without the ability to be re-configured as needed during the process of implanting and attaching to the two opposing rods. While some improvements have been made in the articulation and re-configuration operation of transverse connectors during the implantation and rod connecting process, a continuing need exists to provide a multidirectional articulating transverse connector that can adapt to a wide variance in the contours of the spinal column. Further, a need exists to provide such a transverse connector that can provide sufficient space for the underlying anatomy, most specifically, the dura and spinal cord, while still maintaining a low profile and a smooth contoured surface to thereby reduce the potentially negative impact of the implanted device on the underlying and surrounding soft tissue of the subject into which the device has been surgically implanted.

Conventional efforts to meet this need have fallen short of the desired transverse connector configuration. For example, U.S. Pat. No. 6,554,832, issued to Shluzas, as best seen in FIGS. 2 and 4 of that patent, provides a transverse connector, which includes first and second connector members for connecting to the respective first and second spinal rods. The two connector members are connected one to the other by a connecting rod, which can be withdrawn or extended in alignment with the longitudinal axis of the cross-connector for purpose of adjusting the length thereof. As shown in FIGS. 2 and 4 of the Shluzas patent, the articulation of the connecting members to align with the two opposing spinal rods is limited to a single, centrally disposed ball joint (50). Importantly, the pivoting movement of the Shluzas connector is limited to movement within the same horizontal plane relative to the longitudinal axis of the spinal column. Thus, while the device of Shluzas does permit some limited adjustment in length and azimuth of the device, it is configured to structurally prohibit any upward or downward movement in relation to the surface plane of the spinal column. That is, the elevation of one end of the Shluzas connector relative to the other end of the connector cannot be adjusted. Thus, while the Shluzas design does provide some flexibility in adapting the alignment of the transverse connector to the opposing spinal rods, it falls short of the greater degree of adaptability that could be obtained by a truly multi-planar transverse connector having multiple articulating points. In U.S. Pat. No. 6,110,173, issued to Thomas, more specifically FIGS. 1 and 3, show the rigid nature of the cross connecting rod which does not allow for sufficient space for spinal anatomy. In this regard, the current device affords an improvement in this area as well since the cross-connecting member is arched to allow for such anatomy.

For reasons discussed above a continuing need exists for a transverse connector that provides ease of operation by the surgeon to simultaneously adjust in multiple dimensions one spinal rod connecting end of the connector in relation to the other spinal rod connecting end of the connector and to provide a transverse connector having means for providing sufficient space for spinal anatomy and smooth contours for surfaces in contact with adjacent soft tissue.

SUMMARY

The present disclosure is directed to a transverse connector system including a first spinal rod, a second spinal rod, and a transverse connector. The transverse connector includes a cross member, a first spinal rod connecting member, and a second spinal rod connecting member. The cross member includes opposing first and second ends as well as first and second ball joints disposed at the respective first and second ends. The first and second spinal rod connecting members are secured to the first and second ball joints of the cross member. One or both of the first and second spinal rod connecting members may be configured to articulate in multiple directions about one of the first and second ball joints of the cross member.

Each of the first and second spinal rod connecting members has a compression region. The compression region is configured to selectively and releasably secure to one of the first and second spinal rods. One or more compression slots cooperate with a corresponding ball joint receptacle to define a first compression region.

Each spinal rod connecting member is adapted to receive a locking screw. Each locking screw is operatively coupled to its respective ball joint such that rotation of the locking screw retains the respective spinal rod connecting member in a fixed relationship with the cross member. Rotation of the locking screw fixes the relationship between the respective spinal rod connecting member and the cross member and secures the spinal rod to the respective spinal rod connecting member. Tightening of the locking screw may lock both the spinal rod and the respective ball joint.

Each of the spinal rod connecting members may include first and second compression slots. Each of the first and second compression slots may be dimensioned to pass, one over the other, through a portion of the spinal rod connecting members. The compression slots may have opposing sides of origin and opposing directions of penetration into the spinal rod connecting members. Rotation of the locking screw approximates the opposing sides of origin thereby retaining each of the first and second spinal rod connecting members in the fixed relationship with the cross member.

The first and second spinal rod connecting members each include a spinal rod connecting passage defined between first and second spinal rod retention lips. Each of the first and second spinal rod retention lips project toward one another to an opening to facilitate retention of the spinal rod. One or more of the compression slots originate adjacent to the spinal rod connecting passage such that the one or more compression slots, the first spinal rod retention lip, and the second spinal rod retention lip define a second compression region.

The first and second spinal rod connecting members each define a ball joint receptacle. Each ball joint receptacle may have a lateral opening configured to receive one of the first and second ball joints of the cross member.

The length of the cross member may be selectively adjustable. The cross member may include a curved configuration. The cross member may include an offset cross member providing an offset configuration such that first and second spinal rod connecting members are disposed in a first plane and at least a portion of the offset cross member is disposed in a second plane that is spaced apart and parallel to the first plane.

First and second cross member connecting elements may be secured to the cross member. Each of the first and second cross member connecting elements includes a cross member clamp portion and a linking arm. The linking arm has an articulating ball joint. The first and second cross member connecting elements may include a cross member receptacle that is dimensioned and configured to receive an end of the cross member. The cross member clamp portion of each cross member connecting element includes a top portion, a bottom portion, and a cross member locking screw receptacle that is defined orthogonally through the top and bottom portions. The top and bottom portions are separated by a compression slot defined therebetween. Rotation of the cross member locking screw in a first direction allows one or both of the spinal rod connecting members to move relative to the cross member. Rotation of the cross member locking screw in a second direction fixes one or both of the spinal rod connecting members relative to the cross member.

The cross member may include an insertion arm and a receiving arm. The receiving arm defines a space therein and is configured to receive the insertion arm to thereby adjust the length of the cross member element. One or both of the insertion arm and the receiving arm have a cross member locking screw receptacle configured to receive a cross member locking screw such that rotation of the cross member locking screw exerts pressure against one or both of the insertion arm and the receiving arm to thereby maintain the insertion arm and the receiving arm in a fixed position.

One or both of the first and second ball joints define a recess therein. One or more of the locking screws includes a post extending therefrom. The post is engageable with the recess to retain the respective spinal rod connecting member in a fixed relationship with the cross member and to secure the spinal rod within the compression region. The post and a surface of the recess define a space therebetween when the post and the recess are fully engaged to allow one of the first and second spinal rod connecting members to move slightly relative to one or both of the first and second ball joints through the space such that the respective spinal rod connecting member is in a fixed relationship with the cross member except for the slight movement through the space.

One or both of the spinal rod connecting members defines a receptacle. At least a portion of one of the respective ball joints, an insert, and one of the respective locking screws are positionable within the receptacle to retain the respective spinal rod connecting member in a fixed relationship with the cross member and to secure the spinal rod within the compression region. The respective ball joint defines a recess and the insert includes a post extending therefrom. The post is engageable with the recess when the screw is rotated in a first direction within the receptacle. The engagement of the post and the recess facilitates the retention of the respective spinal rod connecting member in a fixed relationship with the cross member and the securement of the spinal rod within the compression region.

According to one aspect, the present disclosure is directed to a method for securing a transverse connector to a pair of spinal rods. The method includes the step of providing a transverse connector including a cross member, a pair of spinal rod connecting members, and at least one locking screw. The method involves connecting a spinal rod to each spinal rod connecting member, multi-directionally articulating one or both of the spinal rod connecting members relative to the cross member, and rotating the one or more locking screws relative to one of the pair of spinal rod connecting members to fixedly secure one of the spinal rods to the one of the pair of spinal rod connecting members and to fix the one of the pair of spinal rod connecting members in a position relative to the cross member. One step involves adjusting the length of the cross member. The method may include fixing the length of the cross member via a locking screw rotatably secured to the cross member. The method may involve compressing one or both of the spinal rod connecting members by rotating the one or more locking screws relative to one or both of the spinal rod connecting member such that dimensions of compression slots defined within one or both of the spinal rod connecting members are reduced, thereby facilitating the securement of one of the spinal rods within one or both of the spinal rod connecting members.

BRIEF DESCRIPTION OF THE DRAWINGS

The foregoing and other features of the offset transverse connector will become apparent to one skilled in the art to which the disclosed transverse connectors relate upon consideration of the following description of exemplary embodiments with reference to the accompanying drawings, wherein:

FIG. 6A is a perspective view of yet another embodiment of an offset transverse connector, in accordance with the present disclosure;

FIG. 13A is a perspective view of another embodiment of a transverse connector in accordance with the present disclosure;

FIG. 13B is a top view of the transverse connector of FIG. 13A;

FIG. 14B is a side cross-sectional view of the transverse connector of FIG. 14A;

DETAILED DESCRIPTION

Detailed embodiments of the present disclosure are disclosed herein, however, it is understood that the following description and each of the accompanying figures are provided as being exemplary of the disclosure, which may be embodied in various forms without departing from the scope of the present disclosure. Thus, the specific structural and functional details provided in the following description are nonlimiting, but serve merely as a basis for the disclosure as defined by the claims provided herewith.

FIGS. 1A-3B illustrate a transverse connector shown generally as 10. Transverse connector 10 includes first and second spinal rod connecting members 12a and 12b. The spinal rod connecting members 12a and 12b are coupled by a cross member 60.

Figure 1A:
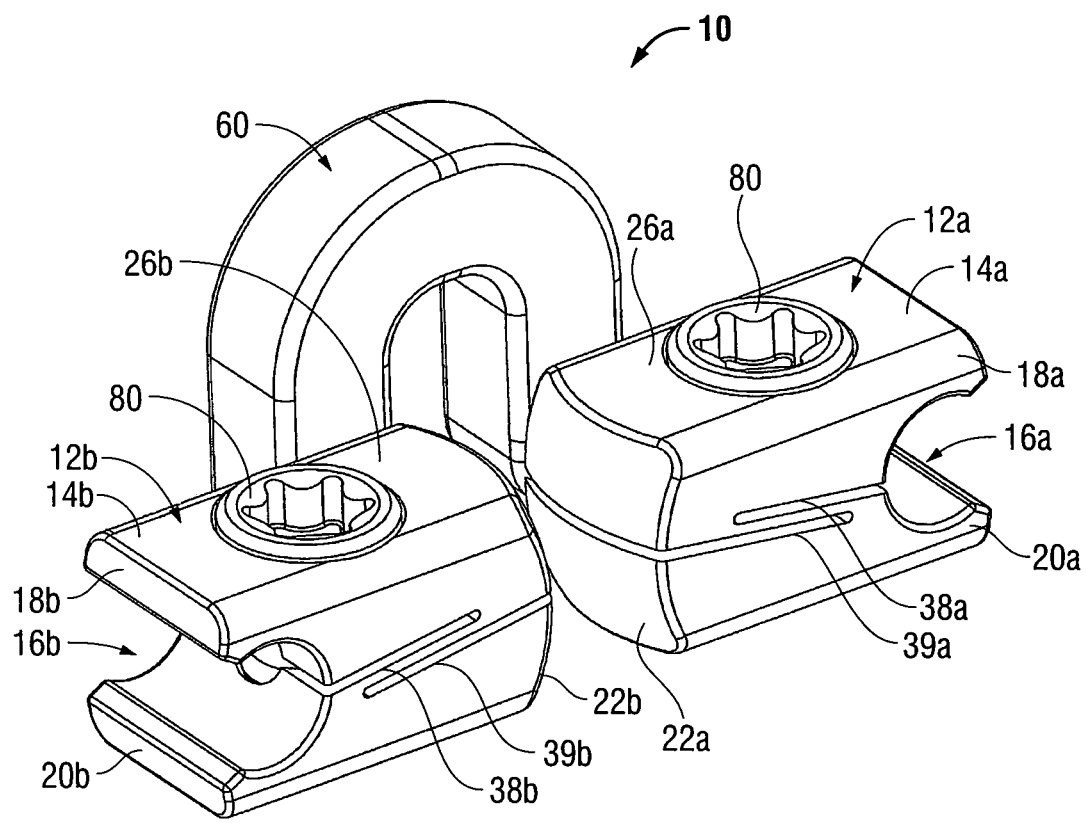
FIG. 1A is a perspective view of an offset transverse connector, in accordance with an embodiment of the present disclosure.
Figure 1B:
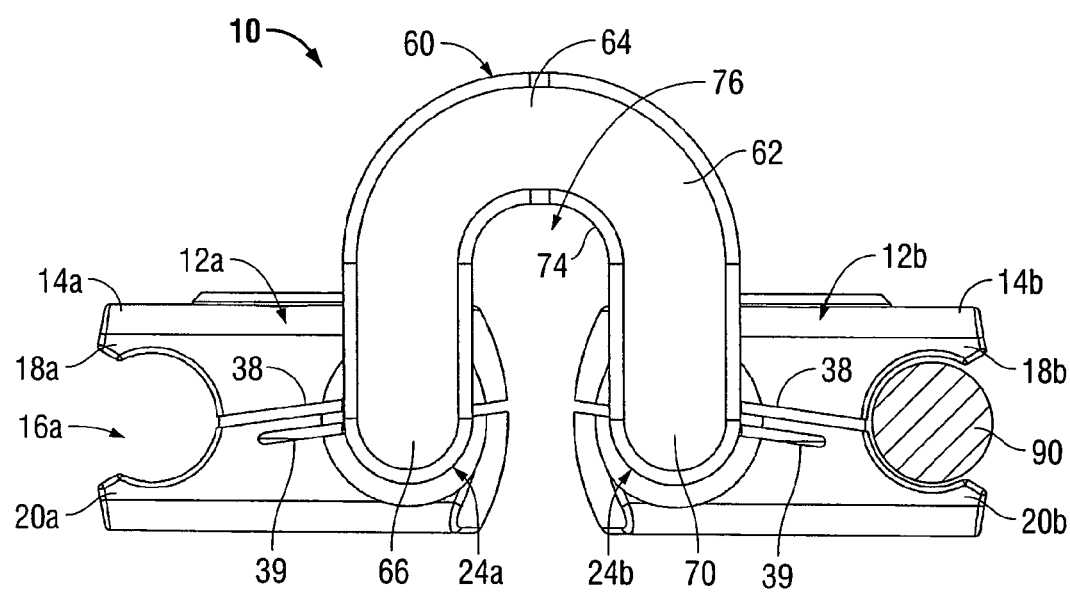
FIG. 1B is an end view of the offset transverse connector of FIG. 1A.

The two spinal rod connecting members 12a and 12b are each configured to be selectively and releasably secured to a spinal rod 90 (as shown in FIG. 1B), which in turn can be secured to the underlying bone of a patient's spinal column as needed. As shown in FIGS. 1A-1D, the spinal rod connecting members 12a and 12b are each configured at their outermost ends 14a and 14b, respectively, of the transverse connector 10 to define first and second spinal rod connecting passages 16a and 16b, the spinal rod connecting passages 16a and 16b being opened medial-laterally at respective first and second ends 14a and 14b of the transverse connector 10. The outermost edges of the respective medial-laterally opened spinal rod connecting passages 14a and 14b may be configured to provide upper spinal rod retention lips 18a and 18b and lower spinal rod retention lips 20a and 20b, each of which projects one toward the other so as to narrow the lateral opening of the spinal rod connecting passages 16a and 16b and to thus facilitate the spinal rod retention capability of the two spinal rod connecting passages 16a and 16b.

The first and second spinal rod connecting members 12a and 12b are each sized and configured at their innermost ends 22a and 22b to define a ball joint receptacle 24, each ball joint receptacles 24 has a lateral opening sized and configured to receive a correspondingly sized ball joint 68 and 72 of cross member 60 in a snap-fit manner.

Figure 1C:
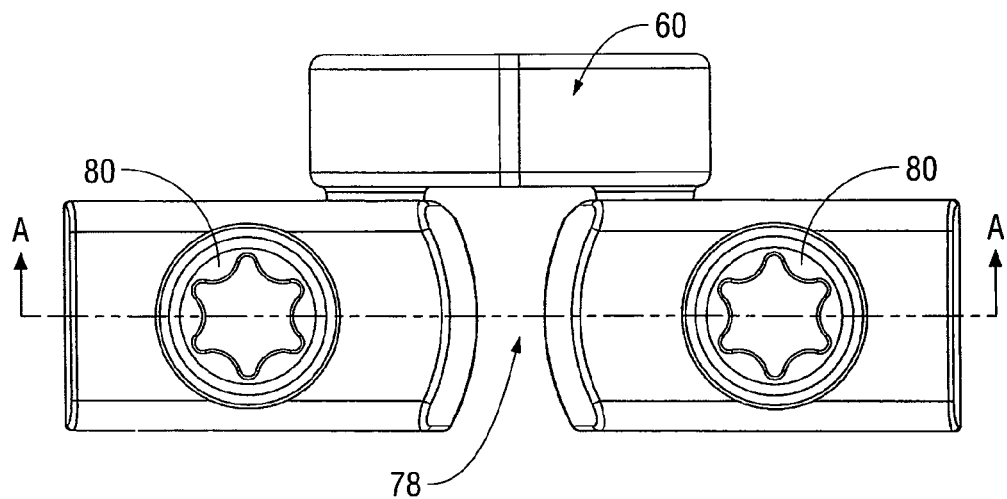
FIG. 1C is a top view of the offset transverse connector of FIG. 1A.
Figure 1D:
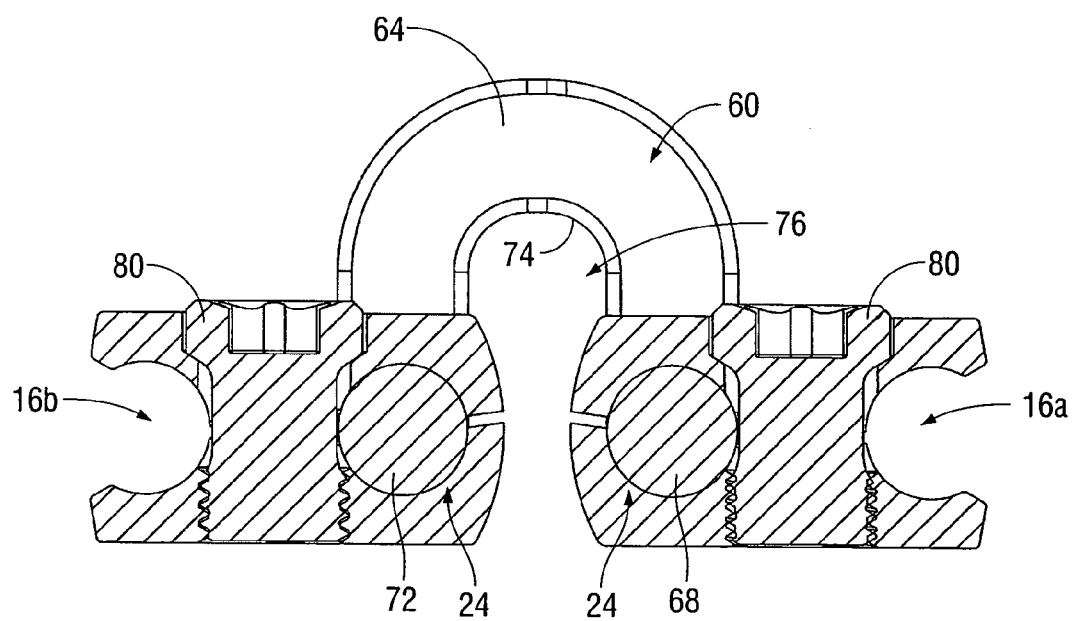
FIG. 1D is a cross-sectional view taken along line A-A in FIG. 1C.

Referring now to FIG. 1B-1D, the cross member 60 includes a cross member element 62 having a U-shaped configuration. Cross member element 62 includes a mid-portion 64, a first end 66 and a second end 70. First end 66 may be configured to provide articulating ball joint 68 and second end 70 may be configured to provide articulating ball joint 72. Cross member element 62 further includes an inner periphery 74 that defines an inner cavity 76 to provide space between first and second spinal rod connecting members 12a and 12b. In addition, cross member 60 provides an offset configuration such that first and second spinal rod connecting members 12a and 12b oppose each other and define a space 78 therebetween, as shown in FIG. 1C.

Figure 2A:
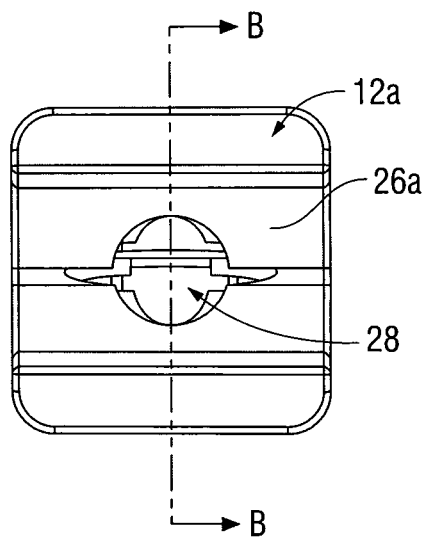
FIG. 2A is a top view of a spinal rod connecting member of the offset transverse connector of FIG. 1A.
Figure 2B:
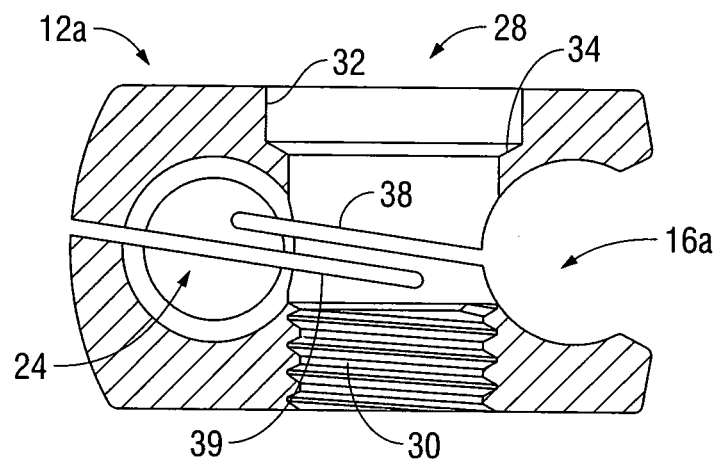
FIG. 2B is a side cross-sectional view taken along line B-B in FIG. 2A.
Figure 3A:
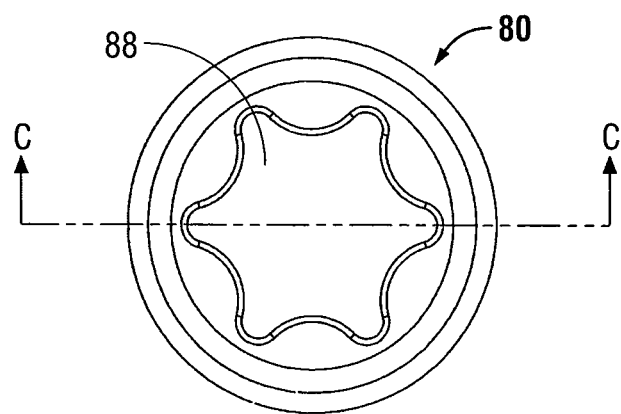
FIG. 3A is a top view of a locking screw of the offset transverse connector of FIG. 1A.
Figure 3B:
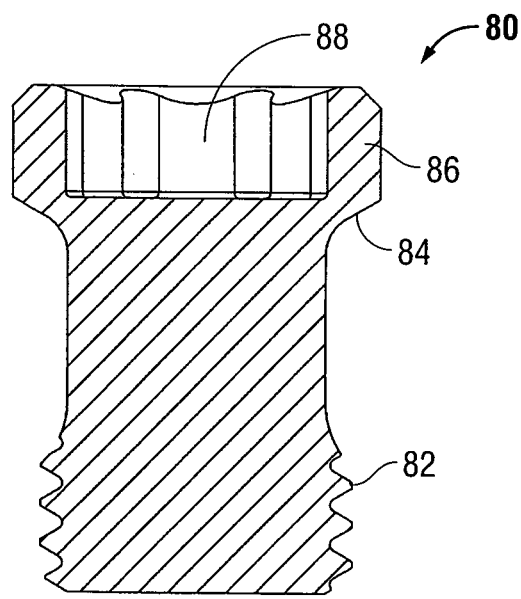
FIG. 3B is a side cross-sectional view taken along line C-C in FIG. 3A.

The features and operation of spinal rod connecting member 12b are substantially identical to spinal rod connecting member 12a and will be omitted in the interest of brevity. Referring now to FIGS. 2A and 2B, spinal rod connecting member 12a includes an upper surface 26a and defines a spinal rod locking screw receptacle 28, which is sized and configured to receive a spinal rod locking screw 80 (as shown in FIGS. 3A and 3B). The spinal rod locking screw receptacle 28, as best shown in FIG. 2B is provided with threads only in a lower portion 30 of receptacle 28. In addition, lower portion 30 of receptacle 28 is provided below the elevation of the spinal rod connecting passages 16a and 16b. An upper portion 32 of spinal rod locking screw receptacle 28 is provided located above the level of the spinal rod connecting passages 16a and 16b and is unthreaded. Upper portion 32 includes an inwardly directed annular restricting ledge 34 that is dimensioned and configured to abut an outwardly directed flange 84 of spinal rod locking screw 80, which will be described further below.

Referring now to FIGS. 3A and 3B, locking screw 80 includes a threaded portion 82 and outwardly directed flange 84 that is provided below a spinal rod locking screw head 86. During use, locking screw 80 is inserted within receptacle 28 of both spinal rod connecting members 12a and 12b (as shown in FIG. 1D), which permits threaded portion 82 of locking screw 80 to pass freely therethrough until threaded portion 82 engages lower threaded portion 30 of the spinal rod locking screw receptacle 28 of both first and second spinal rod connecting members 12a and 12b. In this configuration, as threaded portion 82 of locking screw 80 (as shown in FIG. 1D) is threaded further into threaded portion 30 of receptacle 28, outwardly directed flange 84 on the underside of the spinal rod locking screw head 86 is brought into contact with the inwardly directed annular restricting ledge 34 of the upper portion 32 of receptacle 28.

Spinal rod locking screw 80 further includes a tool cavity 88 so that a clinician may manually screw locking screw 80 with a suitable tool (not shown), for example, but not limited to a screwdriver or a TORX® wrench. As screw 80 is screwed into the threaded portion 30 of the spinal rod locking screw receptacle 28, flange 84 on the underside of screw head 86 exerts compressive forces against the inwardly directed annular restricting ledge 34, as will be described further below.

As shown in FIGS. 1A and 2B, each of spinal rod connecting members 12a and 12b is configured to define first and second compression slots 38 and 39, which from opposing directions in the body of the spinal rod connecting members 12a and 12b can break the external integrity of the members 12a and 12b through the defining wall of the spinal rod connecting passage 28 and the ball joint receptacle 24 of members 12a and 12b. Each compression slot 38, 39 is defined to pass, one over the other, through only a limited portion of the body of the spinal rod connecting members 12a and 12b. By configuring the pair of overlying compression slots 38 and 39 to have opposing sides of origin and, thus, opposing directions of penetration into the body of the spinal rod connecting members 12a and 12b, a connecting member is provided that can react to the above described compressive forces of an inwardly manipulated spinal rod locking screw 80 so as to bring those compressive forces to bear on both the spinal rod connecting passage 28 and the ball joint receptacle 24, which fixes the relationship between spinal rod connecting members 12a and 12b and locks cross member 60 in place. That is, when each locking screw 80 of spinal rod connecting members 12a and 12b is tightened, spinal rod 90 and cross member 60 are locked in a desired position. Thus, by tightening and loosening each locking screw 80 of spinal rod connecting members 12a and 12b, the configuration of transverse connector 10 may be changed. In addition, the compression slots 38, 39 cooperate with the ball joint receptacle 24 to define a first compression region. Further still, the compression slots 38, 39 cooperate with the upper and lower spinal rod retention lips 18, 20 and the spinal rod connecting passage 16 to define a second compression region.

As discussed above and as shown in FIGS. 1A-1D, opposing spinal rod connecting members 12a and 12b are connected to each other by cross member 60. In embodiments, cross member 60 is arched to provide sufficient space for spinal anatomy and therefore not impinge on surrounding tissue or spinal elements.

As shown in the non-limiting examples of FIGS. 1-4, any articulating surface of the transverse connector can be treated, machined, scored, or in any known manner textured to provide a roughened or textured surface that can serve to increase the locking contact of those surfaces when the articulating members are set in place and the associated locking screws are manipulated to lock the transverse connector in the desired configuration.

In operation, a user, as indicated above, can manipulate the transverse connector 10 into a position relative to two opposing and relatively parallel spinal rods, independently connecting the first and second spinal rod connecting members 12a and 12b to their respective spinal rods and adjusting the alignment of the spinal rod connecting members 12a and 12b with the centrally connected cross member 20 by manipulating the respective first ball joint 68 within the ball joint receptacle 24 of spinal rod connecting member 12a and the second ball joint 72 with ball joint receptacle 24 of spinal rod connecting member 12b and selecting the appropriate length of the cross member 60. When all members of the transverse connector 10 are properly positioned, the user can tighten the provided locking screws 80, and lock the transverse connector into a selected configuration relative to the two opposing spinal rods. Adjustment or removal of the transverse connector can be easily achieved by loosening the locking screws 80.

As discussed above, first spinal rod connecting member 12a and second spinal rod connecting member 12b are connected to each other by cross member 60 which terminates at each end 66 and 70 with a respective articulating ball joint 68 and 72. Articulating ball joints 68 and 72 allow cross member 60 to rotatably connect to and articulate with spinal rod connecting members 12a and 12b, as described above. In this embodiment, transverse connector 10 simplifies the insertion and adjustment thereof and provides a fixed length between spinal rods during a surgical procedure.

The above described method of use of the transverse connector 10 can be employed with the use of a plurality of spinal rods 90 and associated bone connecting devices as a method of stabilizing or fixing injured or diseased vertebrae and if necessary, multiple transverse connectors 10 can be employed along the length of the opposing spinal rods 90.

Figure 4A:
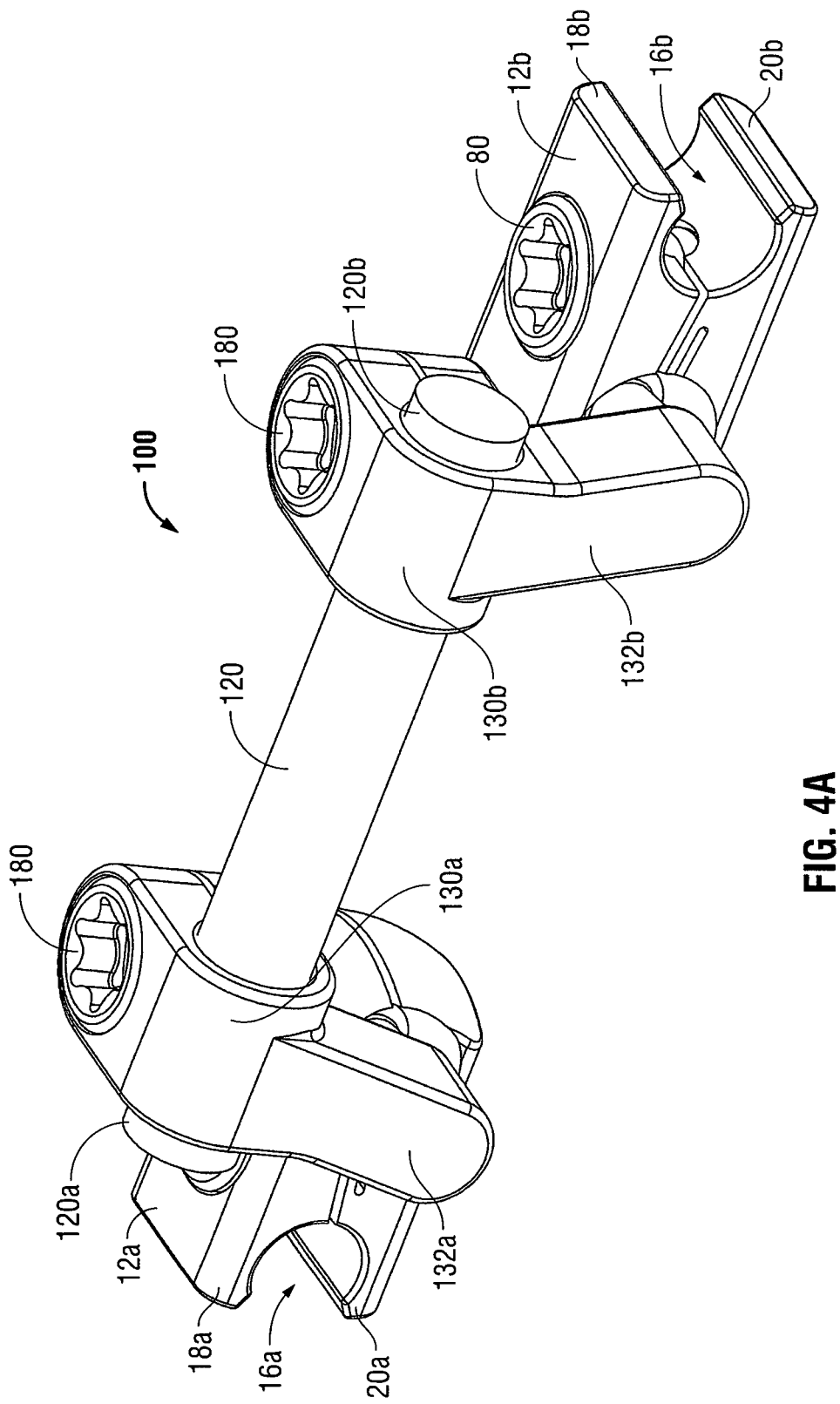
FIG. 4A is a perspective view of another embodiment of an offset transverse connector, in accordance with the present disclosure.
Figure 4B:
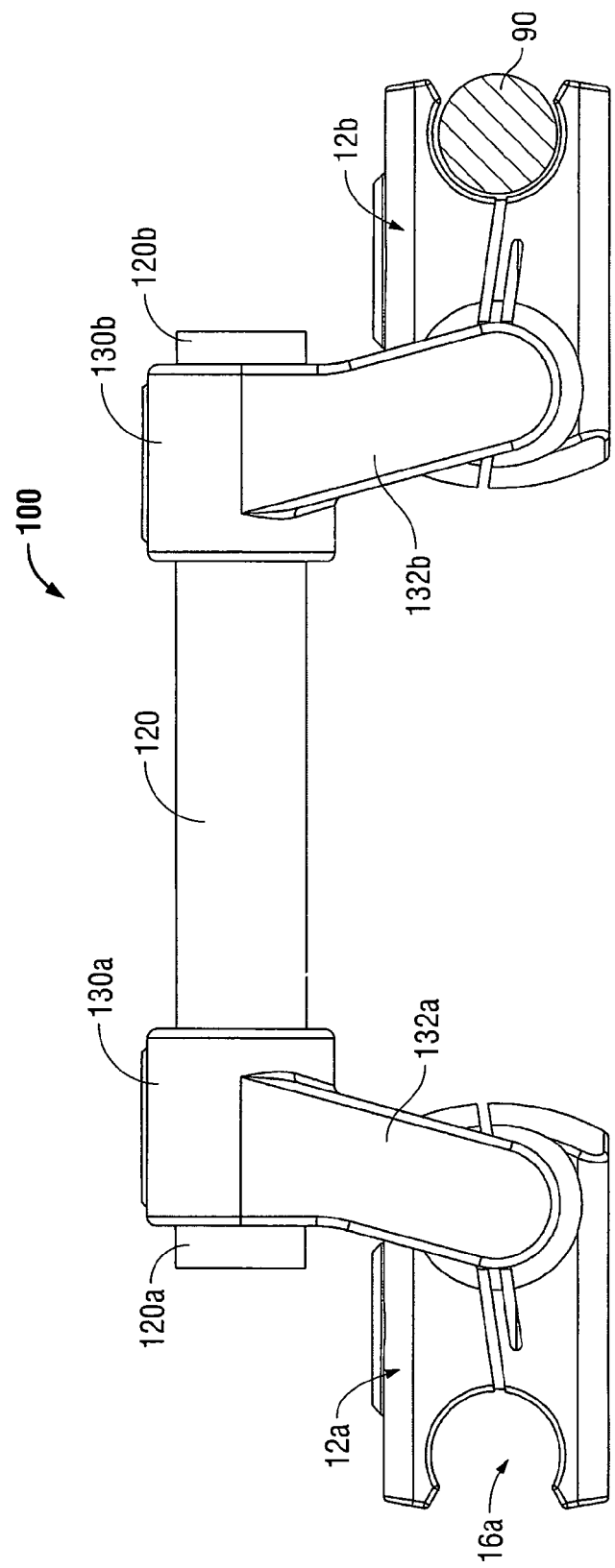
FIG. 4B is an end view of the offset transverse connector of FIG. 4A.
Figure 4C:
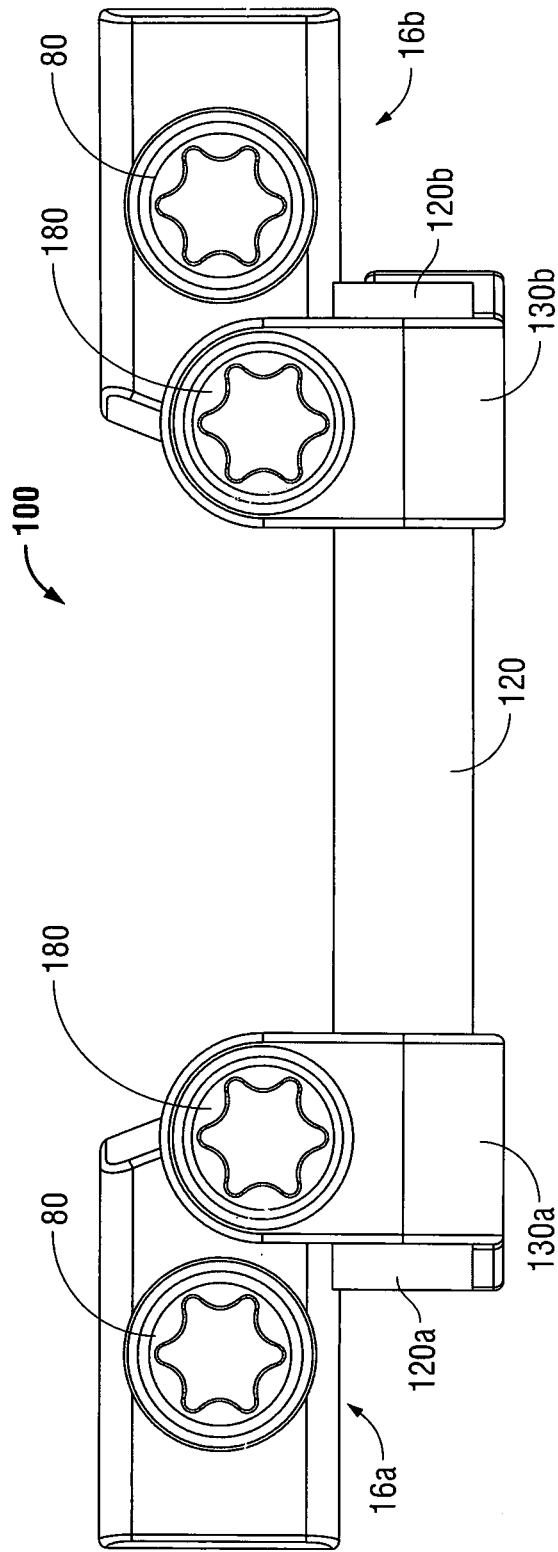
FIG. 4C is a top view of the offset transverse connector of FIG. 4A.

FIG. 4A-4D illustrates another embodiment of the presently disclosed transverse connector shown generally as 100. Transverse connector 100 is similar to other embodiments described herein and therefore is only described herein to the extent necessary to describe the differences in construction and operation thereof. Transverse connector 100 generally includes first and second spinal rod connecting members 12a and 12b for connection to one or more spinal rods 90 (as shown in FIG. 4B). First and second spinal rod connecting members 12a and 12b of transverse connector 100 is substantially similar to the first and second spinal rod connecting members 12a and 12b used with transverse connector 10 and further description thereof will be omitted in the interest of brevity. Transverse connector 100 further includes cross member connecting elements 130a and 130b that are coupled by a cross member element 120, which may be, for example but not limited to a rod. In this embodiment, cross member element 120 allows for adjustment to the length of the transverse connector 100 to custom fit the patient's anatomy. That is, the distance between the cross member connecting elements 130a and 130b may be adjusted to a particular surgical procedure. In still another embodiment, not shown, cross member element 120 may be contoured or bent in order to avoid interference with existing anatomy or aid in the fixation of the transverse connector.

Figure 4D:
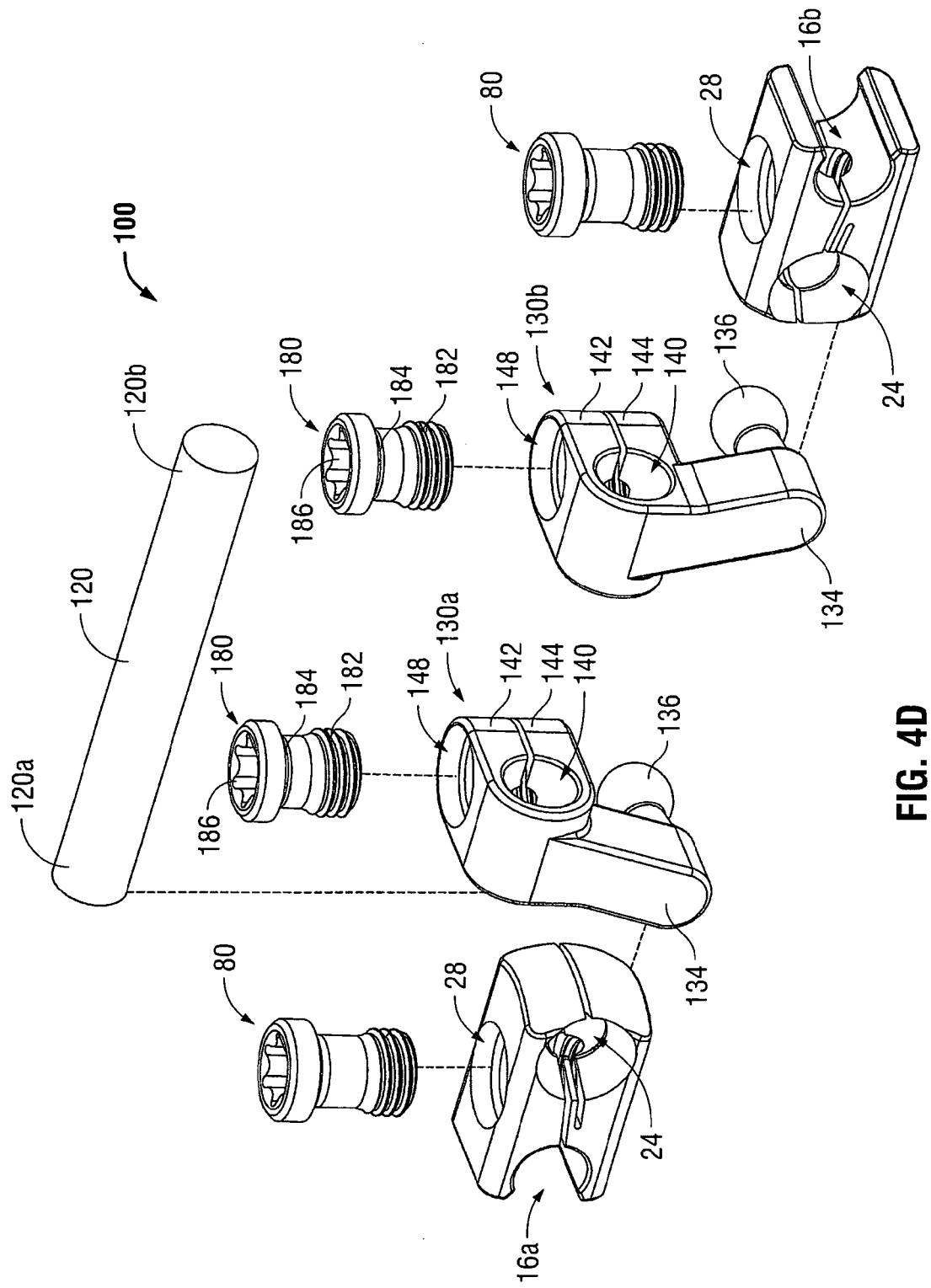
FIG. 4D is an exploded view, with parts separated, of the offset transverse connector of FIG. 4A.
Figure 5:
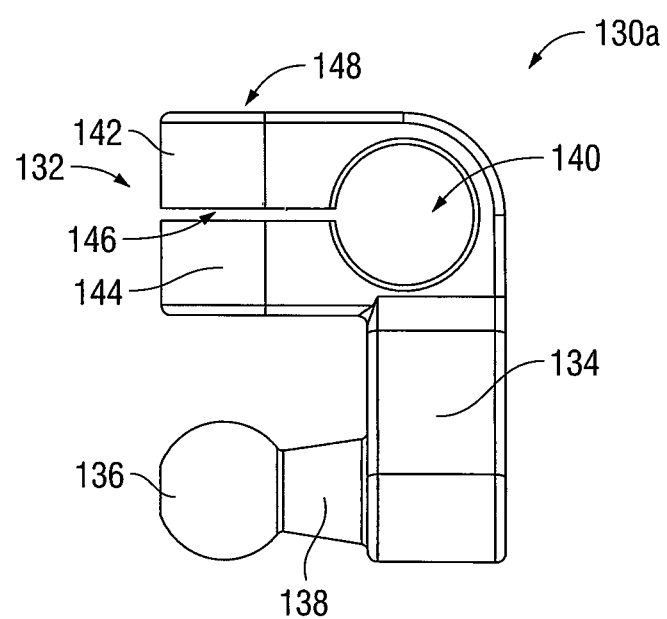
FIG. 5 is a side view of a cross member connecting element of the offset transverse connector of FIG. 4A.

Referring now to FIG. 5 in conjunction with FIGS. 4A-4D, first and second cross member connecting elements 130a and 130b are provided and include a cross member clamp portion 132, a linking arm 134 coupled to an articulating ball joint 136. Articulating ball joint 136 is connected to linking arm 134 by a connecting member 138. Ball connecting member 138 may have a conical tapered configuration. For example, ball connecting member 138 may taper from a large radius to a smaller radius from linking arm 134 to articulating ball joint 136. First and second cross member connecting elements 130a and 130b further include a cross member receptacle 140 that is dimensioned and configured to receive a first end 120a or a second end 120b of cross member element.

Cross member clamp portion 132 of each cross member connecting element 130a, 130b includes a top portion 142, a bottom portion 144 and a cross member locking screw receptacle 148 that is defined orthogonally through top portion 142 and bottom portion 144. Top portion 142 and bottom portion 144 are separated by a compression slot 146 that is defined therebetween.

As shown in FIG. 4D, cross member locking screws 180 are similar to locking screws 80, however, locking screws 180 may be shorter in length so as to fit within screw receptacle 148 of clamp portion 132 of each cross member connecting element 130a, 130b. Locking screw 180 includes a threaded portion 182, an outwardly facing flange portion 184 and a tool cavity 186 for removal of the screw thereof. Upon insertion of the cross member locking screw 180 within cross member locking screw receptacle 148, compression slot 146 is compressed such that top portions and portions 142 and 144 are approximated towards each other. In this manner, an inner dimension of cross member receptacle 148 decreases in size, for example, its diameter, to thereby retain cross member 120 in a compressed configuration.

Referring now to FIGS. 6A-6F, another embodiment of a transverse connector is shown and generally depicted as 200. Transverse connector 200 is similar to other embodiments described herein and therefore is only described herein to the extent necessary to describe the differences in construction and operation thereof. Transverse connector 200 includes an arcing cross member 220, spinal rod connecting members 230, and a cross member locking screw 280. In embodiments, cross member 220 is arched to provide sufficient space for spinal anatomy and therefore not impinge on surrounding tissue or spinal elements.

Figure 9A:
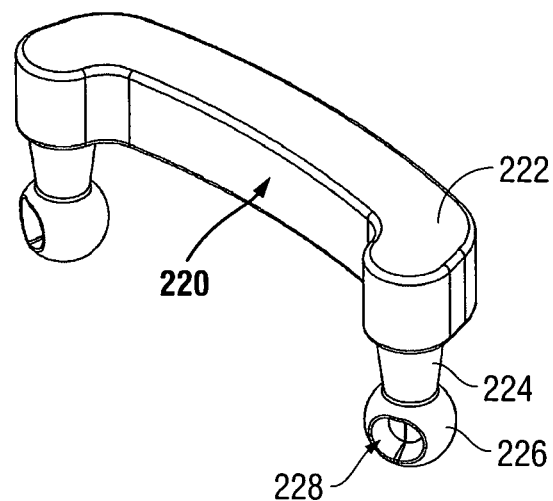
FIG. 9A is a perspective view of a cross-member of the offset transverse connector of FIG. 6A.
Figure 9B:
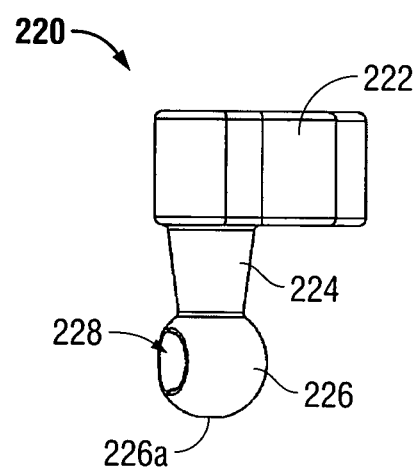
FIG. 9B is a side view of the cross member of FIG. 9A.

Referring to FIGS. 9A and 9B, arcing cross member 220 includes a ball joint 226 on each end 222, respectively, that is connected by a ball connecting member 224. Ball connecting member 224 may have a conical tapered configuration. For example, ball connecting member 224 may taper from a larger radius to a smaller radius from end 222 to ball joint 226. Each ball joint 226 includes a recess 228 that will be described further below.

Figure 6B:
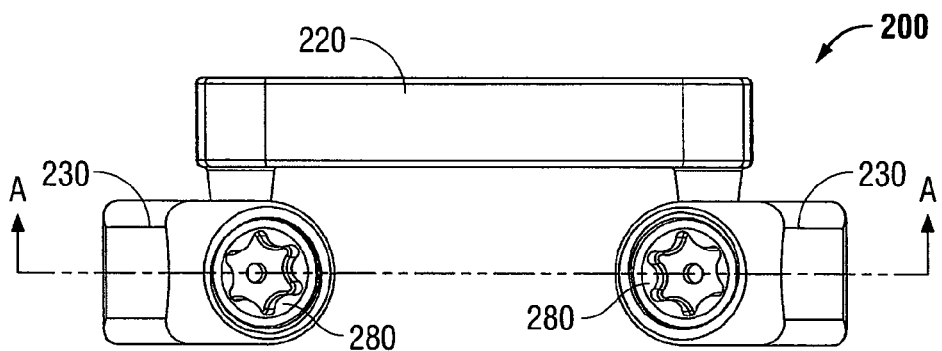
FIG. 6B is a top view of the offset transverse connector of FIG. 6A.
Figure 6C:
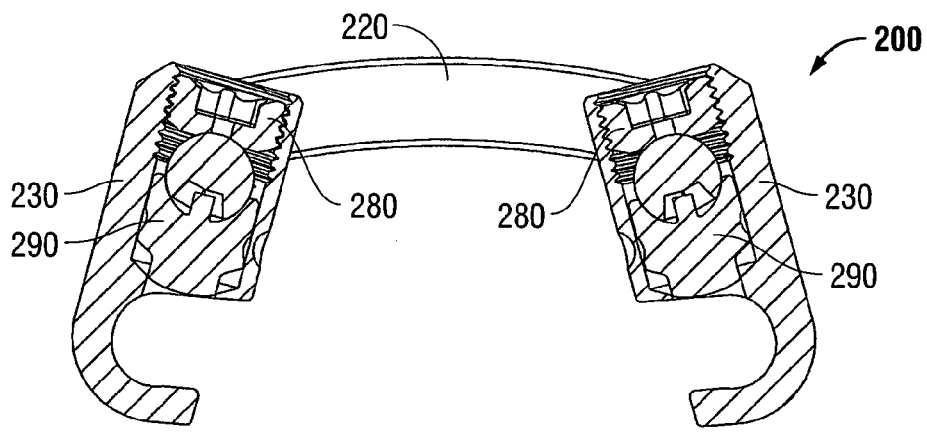
FIG. 6C is a side cross-sectional view taken along line A-A in FIG. 6B.
Figure 6D:
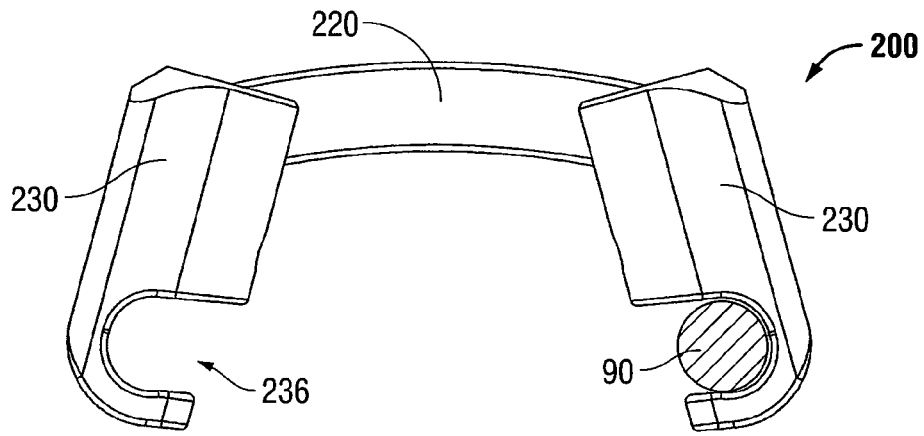
FIG. 6D is an end view of the offset transverse connector of FIG. 6A.
Figure 6E:
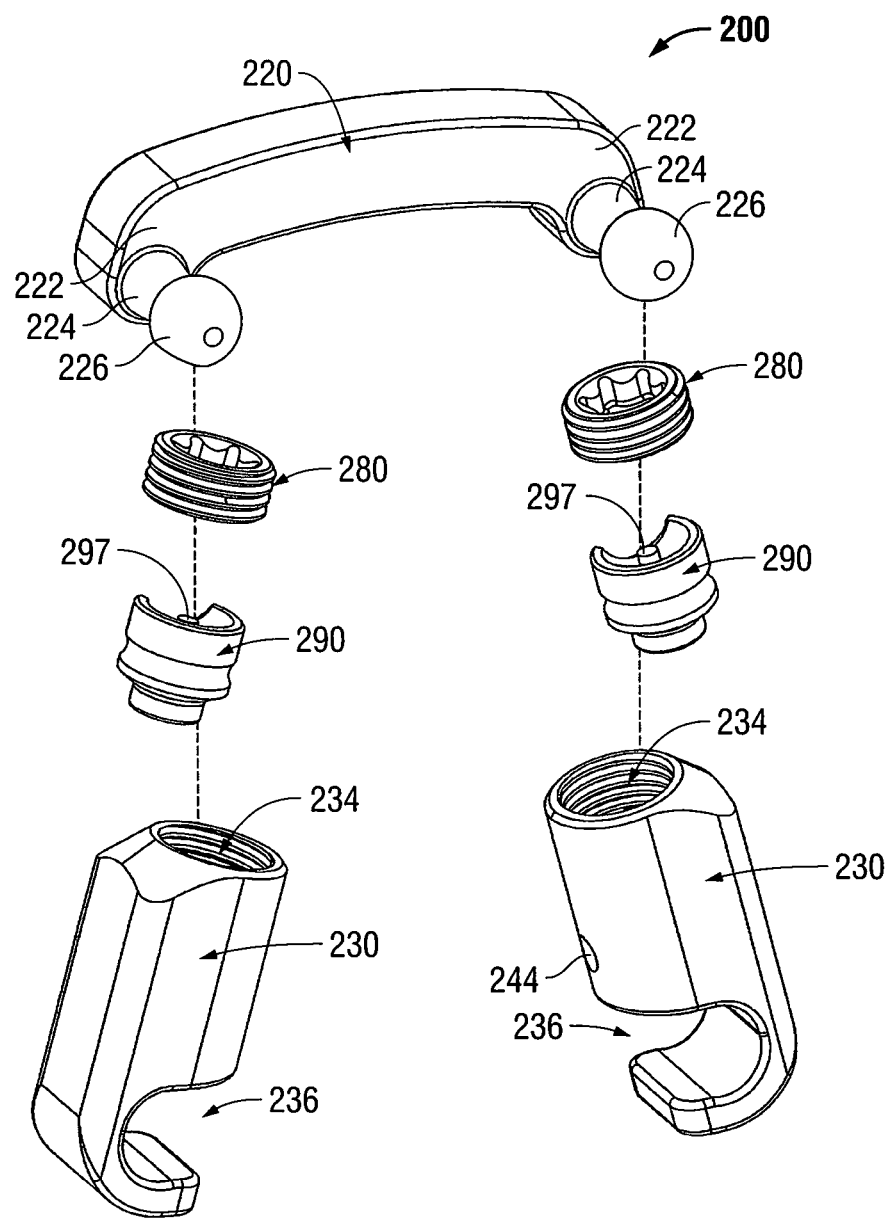
FIG. 6E is an exploded view, with parts separated, of the offset transverse connector of FIG. 6A.
Figure 7A:
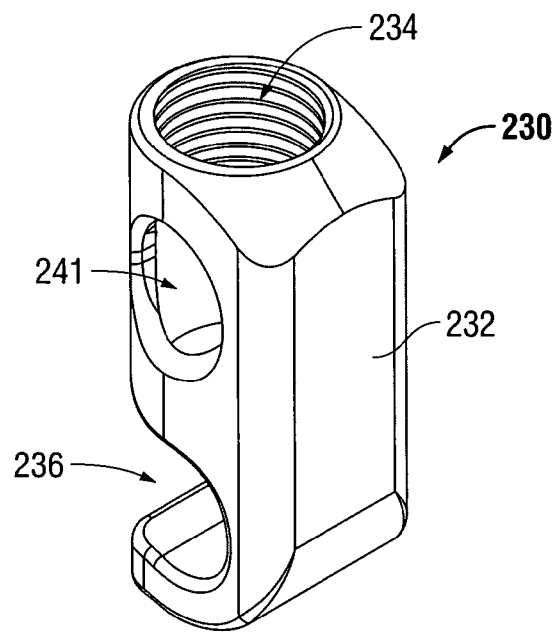
FIG. 7A is a perspective view of a spinal rod connecting member of the offset transverse connector of FIG. 6A.
Figure 7B:
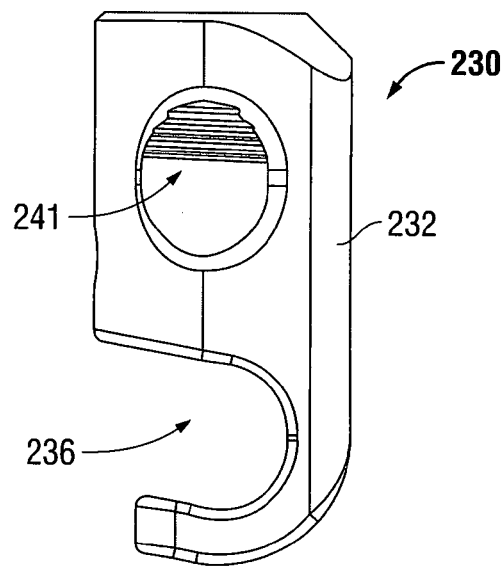
FIG. 7B is an end view of the spinal rod connecting member of FIG. 7A.
Figure 7C:
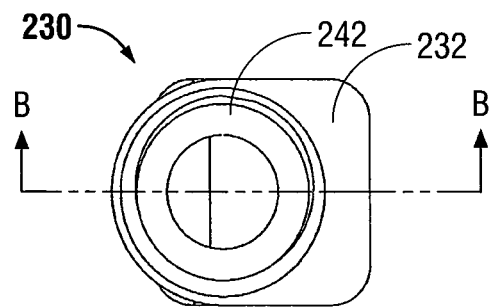
FIG. 7C is a top view of the spinal rod connecting member of FIG. 7A.
Figure 7D:
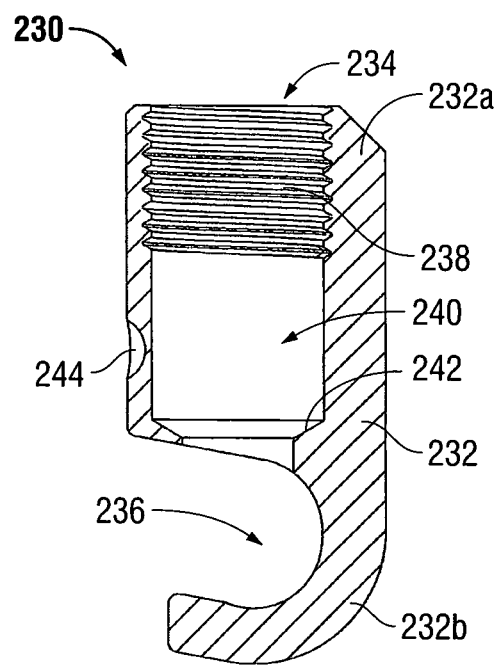
FIG. 7D is a side cross-sectional view taken along line B-B in FIG. 7C.

Referring now to FIGS. 7A-7D in conjunction with FIGS. 6A-6D, a spinal rod connecting member 230 is shown including a body 232 having a top portion 232a and a bottom portion 232b. Top portion 232a defines a cross member locking screw receptacle 234 and bottom portion 232b defines a spinal rod passage 236 adapted to receive and contain a spinal rod 90 (as shown in FIG. 6D). Cross member locking screw receptacle 234 includes threads 238 along its periphery, an inner cavity 240, a ball joint receptacle 241, and an inwardly facing ledge 242 at the bottom surface of inner cavity 240. In embodiments, spinal rod connecting member 230 may also include an aperture 244 for reception of a screw (not shown) to facilitate retaining of an insert 290 (FIGS. 10A-10B), which will be described further below.

Figure 8A:
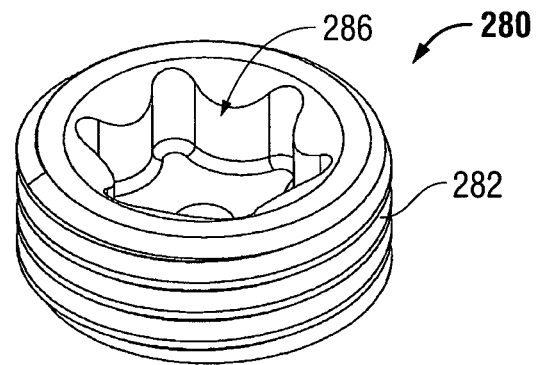
FIG. 8A is a perspective view of a locking screw of the offset transverse connector of FIG. 6A.
Figure 8B:
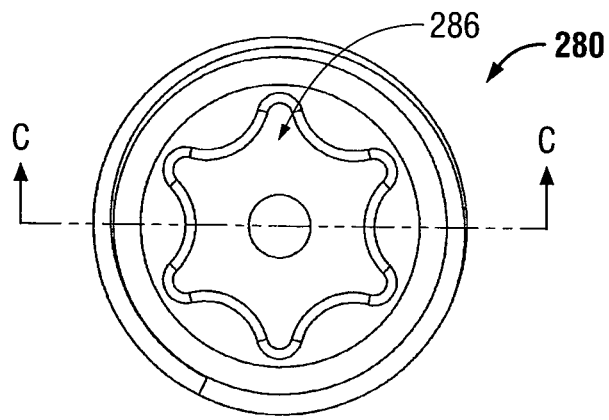
FIG. 8B is a top view of the locking screw of FIG. 8A.
Figure 8C:
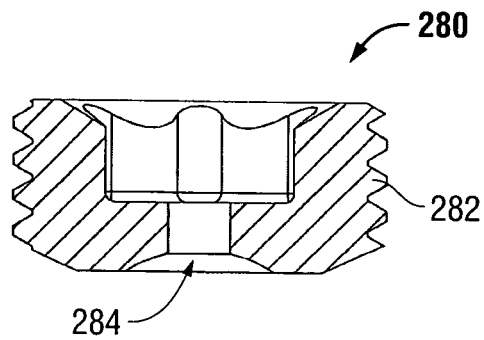
FIG. 8C is a side cross-sectional view taken along line C-C in FIG. 8B.

Referring now to FIGS. 8A-8C, a locking screw 280 includes a threaded portion 282 and a concave cavity 284 that is provided below the threaded portion 282 and on an underside of locking screw 280. In embodiments, concave cavity 284 may be dimensioned to have a substantially perfect fit with an arcuate top portion of ball joint 226. Spinal rod locking screw 280 further includes a tool cavity 286 so that a clinician may manually screw locking screw 280 with a suitable tool (not shown), for example, but not limited to a screwdriver or a TORX® wrench.

Figure 10A:
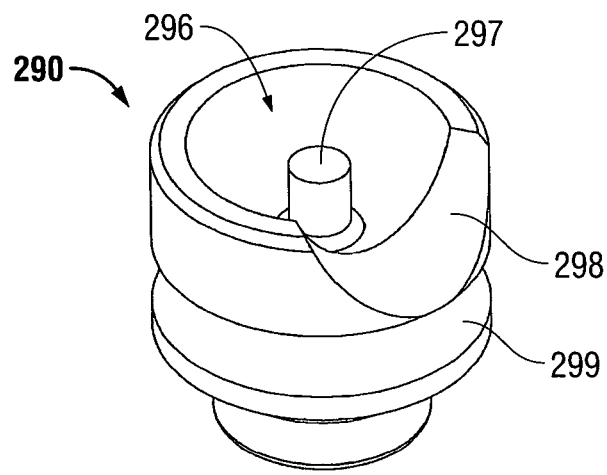
FIG. 10A is a perspective view of an insert of the offset transverse connector of FIG. 6A.
Figure 10B:
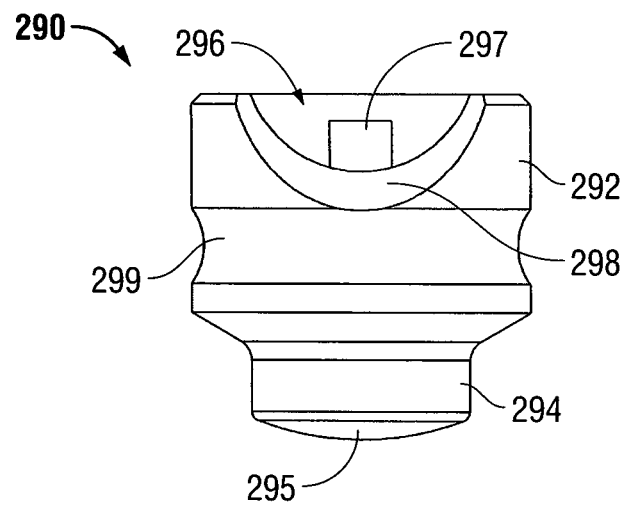
FIG. 10B is a side view of the insert of FIG. 9A.

Referring now to FIGS. 10A and 10B, an insert 290 is shown to include a top portion 292 and a bottom portion 294 that is dimensioned to have a curved bottom surface 295. Top portion 292 includes a concave cavity 296 and a post 297 that is provided in the center of the cavity 296. Concave cavity 296 is configured to receive a bottom portion of ball joint 226 during assembly. A saddle 298 is provided alongside a segment of top portion 292. Saddle 298 defines a space that is configured to receive ball connecting member 224 when ball joint 226 is sandwiched between screw 280 and insert 290.

Insert 290 further includes a radial groove 299 that is annularly defined alongside a middle portion thereof. In embodiments, radial groove 299 is configured to receive a screw (not shown) via aperture 244 such that the screw may retain insert 290 at a certain position in a compressive fashion.

During use and assembly of transverse connector 200 and referring back to FIG. 6F, insert 290 is positioned within inner cavity 240 of locking screw receptacle 234 such that curved bottom portion 295 abuts inwardly facing ledge 242 of inner cavity 240. Subsequently, ball joints 226 of cross member 220 are positioned within their respective ball joint receptacles 241, while inserts 290 are configured and adjustably turned such that saddles 298 provide a securing seat for their respective ball connecting members 224. In addition, post 297 of insert 290 loosely fits within recess 228 of ball joint 226 to provide predefined amount of rotation of ball joint 226 within ball joint receptacle 241, while a bottom portion 226a of ball joint 226 is seated within concave cavity 296 of insert 290.

Subsequently, locking screw 280 is placed and rotated (e.g., screwed) into the threaded portion 238 of locking screw receptacle 238, while concave cavity 284 on the underside of screw 280 exerts compressive forces against the convex top portion of ball joint 226. At the same time, bottom portion 226a of ball joint 226 exerts compressive forces against the top portion 292 of insert 290. That is, the bottom arcuate portion of ball joint 226 abuts the top arcuate cavity of insert 290. As discussed above, recess 228 of ball joint 226 is configured to receive post 297 of top portion 292, which thereby constricts the articulating movement of ball joint 226 to a limited amount of movement and adjustment. In this configuration, as threaded portion 282 of locking screw 280 is threaded further into threaded portion 238 of receptacle 234, bottom portion 226a of ball joint 226 exerts compressive forces against the top portion 292 of insert 290, which in turn 295 on the underside of insert 290 is brought into contact with the inwardly directed annular restricting ledge 242 of inner cavity 240 of receptacle 234 to create a tight fit.

It is envisioned that transverse connector 200 provides a low profile means for attaching to the rod, such that none of the transverse connector compromises the anatomy (dura and spinal cord) that resides between the rods. It is also envisioned that this embodiment still provides the ball joint feature as means of attachment of the cross member to the spinal rod attaching member, which allows for at least 3 degrees of freedom for attachment. In addition, this embodiment still allows for various lengths of cross member 220 to accommodate various sized patients. Spinal rod connecting member 230 is biased laterally with respect to cross member 220 so as to provide the maximum amount of space possible for critical anatomical structures (dura and spinal cord). As discussed above, cross member 220 may also be designed to have an adjustable length or can come in various predetermined lengths to accommodate patient anatomy.

Figure 11A:
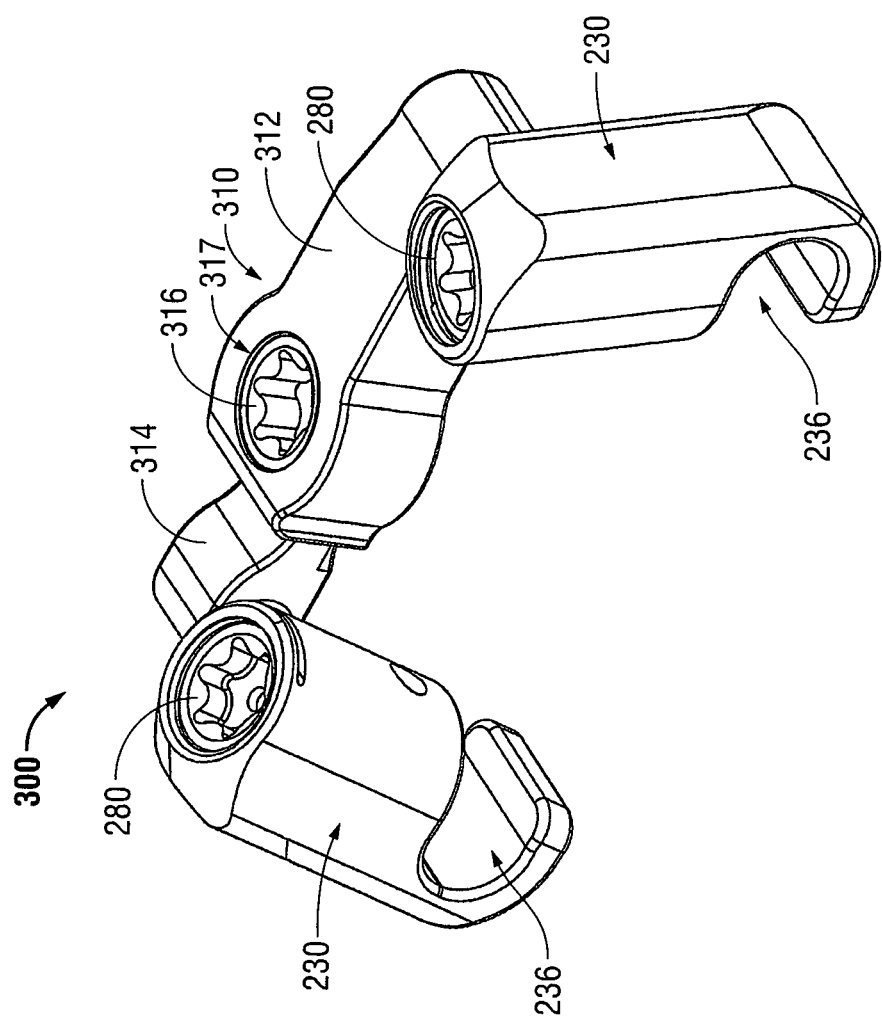
FIG. 11A is a perspective view of another embodiment of an offset transverse connector, in accordance with the present disclosure.
Figure 11B:
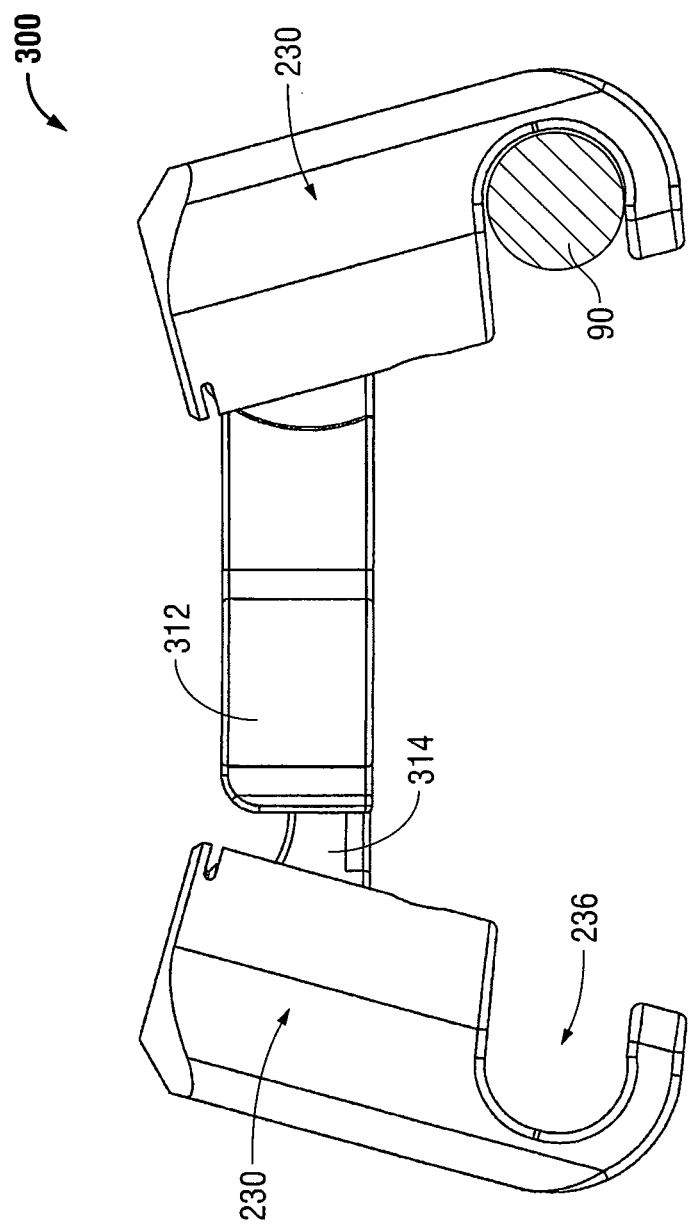
FIG. 11B is an end view of the offset transverse connector of FIG. 11A.
Figure 11C:
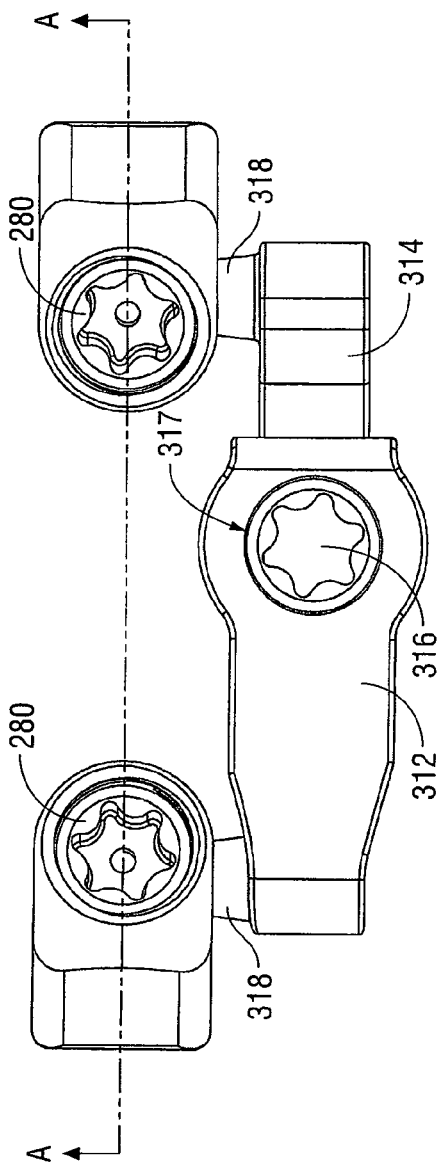
FIG. 11C is a top view of the offset transverse connector of FIG. 11A.

Referring now to FIGS. 11A-11D, another embodiment of a transverse connector is shown and generally depicted as 300. Transverse connector 300 is similar to other embodiments described herein and therefore is only described herein to the extent necessary to describe the differences in construction and operation thereof. Transverse connector 300 includes an adjustable cross member 310, spinal rod connecting members 230, and a cross member locking screw 280. In embodiments, cross member 310 is offset from spinal rod connecting members 230 to provide sufficient space for spinal anatomy and to therefore not impinge on surrounding tissue or spinal elements. Transverse connector 300 includes spinal rod connecting member 230, similar to transverse connector 200, which defines a spinal rod passage 236 adapted to receive and contain a spinal rod 90 (as shown in FIG. 11B). Spinal rod connecting member 230 of transverse connector 300 is substantially similar to the spinal rod connecting member 230 used with transverse connector 200, thus further description thereof will be omitted in the interest of brevity.

Figure 11D:
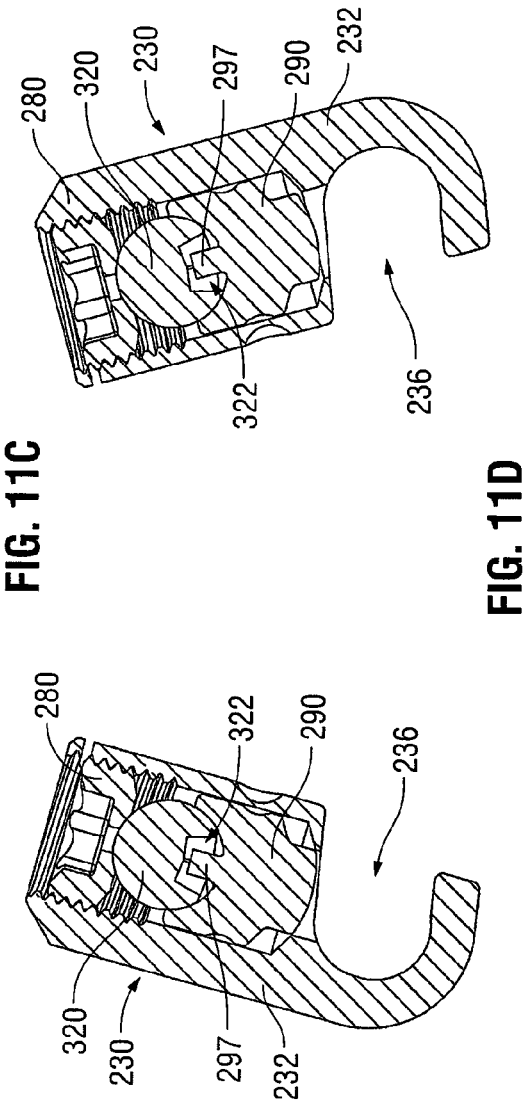
FIG. 11D is a side cross-sectional view taken along line A-A in FIG. 11C.

Adjustable cross member 310 includes a receiving arm 312, an insertion arm 314, a cross member locking screw 316 and a cross member locking screw receptacle 317. During use, as cross member locking screw 316 is tightened, cross member locking screw 316 is configured to exert pressure against insertion arm 314 to maintain insertion arm 314 at a specific position. In this manner, adjustable cross member 310 may be adjusted to a desired length in accordance to a surgeon's specification by loosening and tightening cross member locking screw 316. Adjustable cross member 310 is connected to spinal rod connecting member 230 in a similar manner as arcing cross member 220 is connected to spinal rod connecting member 230, as described above. For example, adjustable cross member 310 includes a ball joint 320 on each arm 312 and 314, respectively, that is connected by a ball connecting member 318. As shown in FIG. 11D, each ball joint 320 defines a recess 322 that is disposed within a cross member locking screw receptacle 234. In this configuration, recess 322 of ball joint 320 is configured to receive a post 297 of an insert 290 in a similar fashion as described above. Spinal rod connecting member 230 of transverse connector 300 is substantially similar to the spinal rod connecting member 230 used with transverse connector 200, described above, thus further description thereof will be omitted in the interest of brevity.

Referring now to FIGS. 12A-12D, another embodiment of a transverse connector is shown and generally depicted as 400. Transverse connector 400 is similar to other embodiments described herein and therefore is only described herein to the extent necessary to describe the differences in construction and operation thereof. Transverse connector 400 includes a receiving arm assembly 410, an insertion arm assembly 430, and a spinal rod connecting member 450. As can be appreciated, the receiving arm assembly and the insertion arm assembly collectively define a cross member, as discussed above with respect to some of the other embodiments.

Receiving arm assembly 410 includes a receiving arm 412 and a receiving aim extension 414 having an articulating ball joint 418 connected via a ball connecting member 416. Ball joint 418 includes a top surface 418a that defines a recess 418b. Receiving arm assembly 410 further includes receiving arm guides 420a and 420b that define an opening 422 therebetween and configured to receive insertion arm assembly 430.

Insertion arm assembly 430 includes an insertion arm 432 and an insertion arm extension 434 having an articulating ball joint 438 connected via a ball connecting member 436. Similar to ball joint 418, ball joint 438 includes a top surface 438b that defines a recess 438a. Insertion arm 432 includes a screw receptacle 440 having threads 442 disposed alongside an inner periphery therewithin for receiving an insertion arm locking screw 490.

Figure 12A:
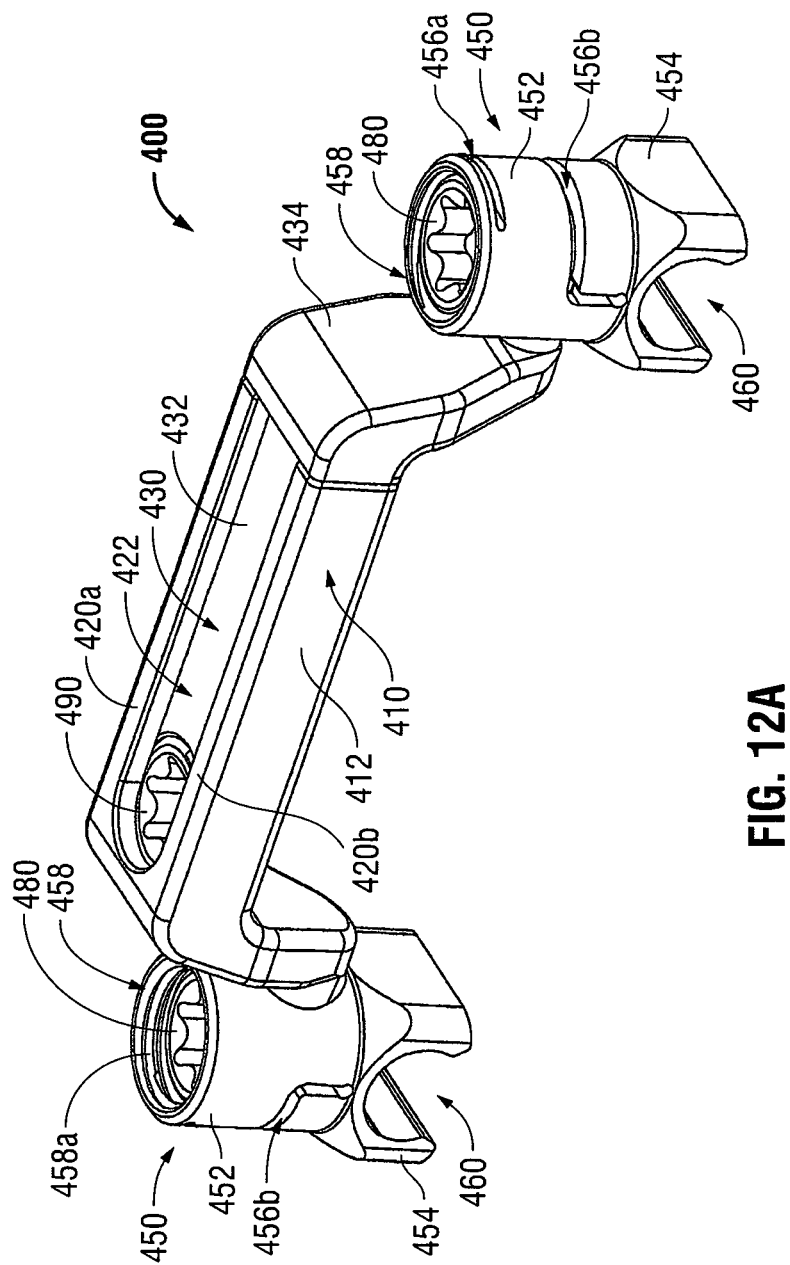
FIG. 12A is a perspective view of yet another embodiment of an offset transverse connector, in accordance with the present disclosure.
Figure 12B:
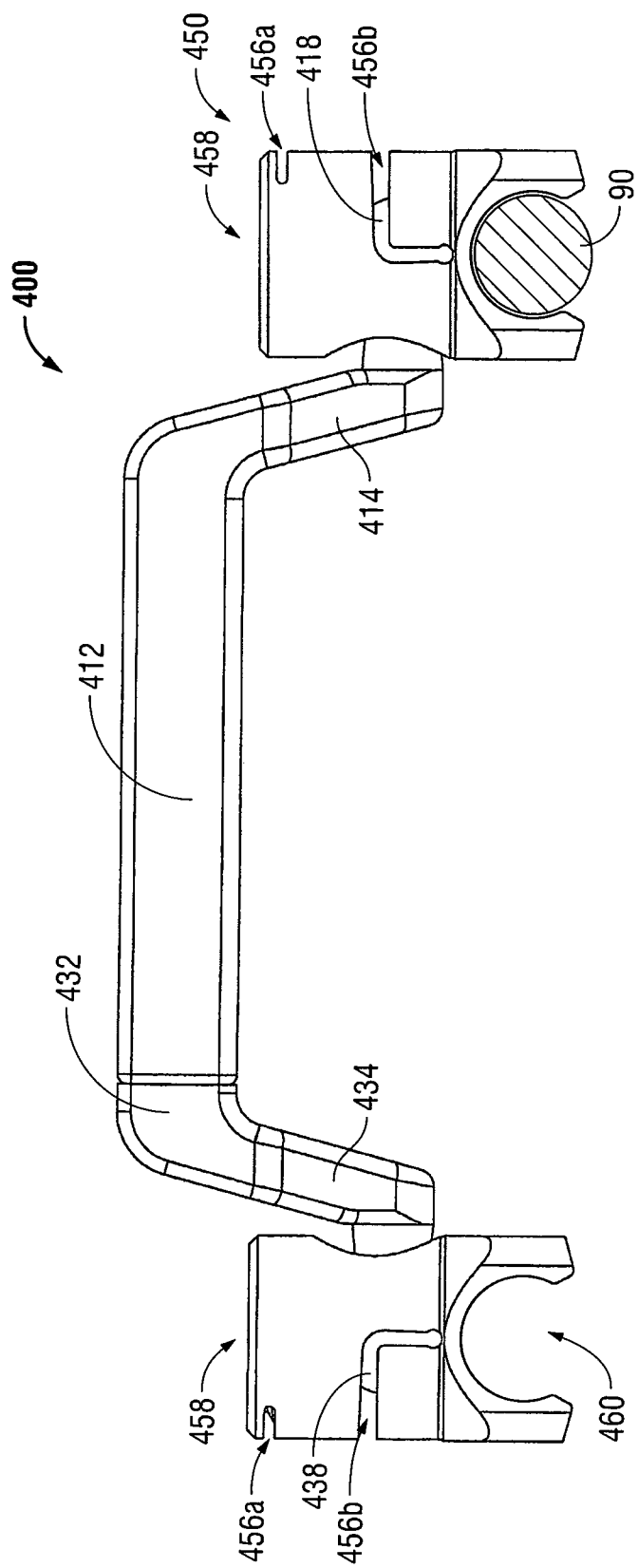
FIG. 12B is an end view of the offset transverse connector of FIG. 12A.
Figure 12C:
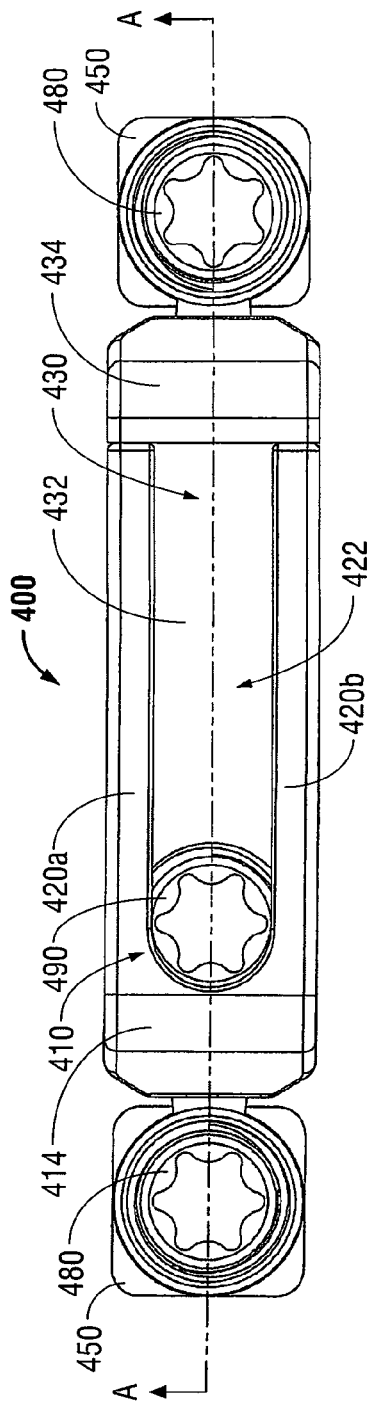
FIG. 12C is a top view of the offset transverse connector of FIG. 12A.
Figure 12D:
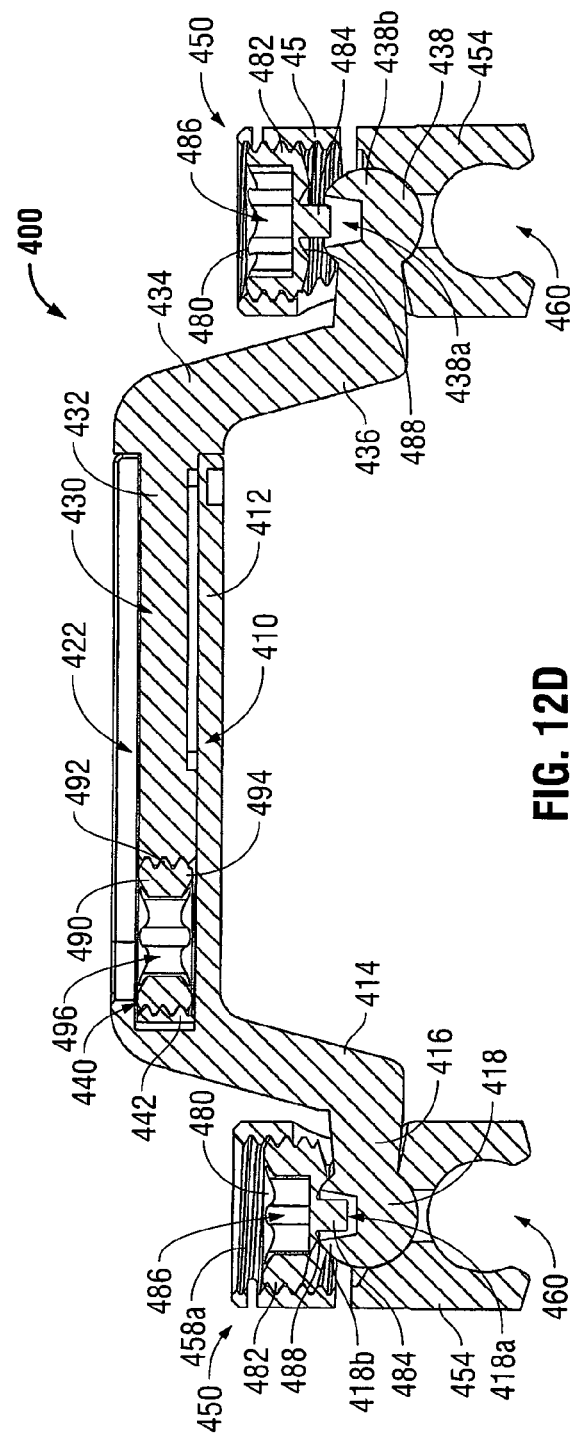
FIG. 12D is a side cross-sectional view taken along line A-A in FIG. 12C.

Referring to FIG. 12D, insertion arm locking screw 490 is shown having threads 492, a bottom surface 494, and a tool cavity 496 so that a clinician may manually screw locking screw 480 with a suitable tool (not shown).

Spinal rod connecting member 450 includes a top portion 452 and a bottom portion 454, which each define compression slots 456a and 456b, respectively (as shown in FIG. 12B). Spinal rod connecting member 450 further includes a locking screw receptacle 458 having a threaded surface 458a that is configured to receive a cross member connection locking screw 480, as will be described further below. Each spinal rod connecting member 450 defines a spinal rod connecting passage 460 that is provided on a bottom portion of spinal rod connecting member 450. Spinal rod connecting passage 460 is configured to receive and securely retain a spinal rod 90 (as shown in FIG. 12B).

Still referring to FIG. 12D, cross member connecting locking screw 480 is shown having threads 482 alongside of locking screw 480. On a top portion, locking screw 480 includes a tool cavity 486 so that a clinician may manually screw locking screw 480 with a suitable tool (not shown), for example, but not limited to a screwdriver or a TORX® wrench. On a bottom portion, locking screw 480 includes a concave cavity 488 and a post 484 that is provided in the center of the concave cavity 488. Post 484 is configured to be inserted within recess 438a of top surface 438b of ball joint 438 during assembly to provide a friction fit.

During use and assembly of transverse connector 400 and referring back to FIG. 6F, locking screw 480 is positioned within locking screw receptacle 458 such that concave cavity 488 and post 484 is positioned within recess 438a of top surface 438b of ball joint 438 during assembly to provide a friction fit.

Subsequently, as locking screw 480 is placed and rotated (e.g., screwed) into locking screw receptacle 458, concave cavity 488 and post 484 on the underside of screw 480 exert compressive forces against and within recess 438a of top surface 438b of ball joint 438 during assembly to provide a friction fit.

It is envisioned that transverse connector 400 provides a low profile means for attaching to the rod, such that none of the connector compromises the anatomy (dura and spinal cord) that resides between the rods. It is also envisioned that this embodiment still provides the ball joint feature as means of attachment of the cross member to the spinal rod attaching member, which allows for at least 3 degrees of freedom for attachment. In addition, this embodiment still allows for various lengths of receiving arm assembly 410 and insertion arm assembly 430 to accommodate various sized patients. Spinal rod connecting member 450 is biased laterally with respect to receiving arm assembly 410 and insertion arm assembly 430 so as to provide the maximum amount of space possible for critical anatomical structures (dura and spinal cord).

Turning now to FIGS. 13A-13D, another embodiment of a transverse connector is shown which is generally referred to as transverse connector 500. Transverse connector 500 is similar to other embodiments described herein and therefore is only described herein to the extent necessary to describe the differences in construction and operation thereof. Transverse connector 500 includes a pair of substantially identical spinal rod connection members 550. One of the pair of spinal rod connection members 550 is secured to a receiving arm assembly 510 and the other of the pair of the spinal rod connection members 550 is secured to an insertion arm assembly 530. The receiving arm assembly 510 and the insertion arm assembly 530 are slidably disposed relative to one another between the pair of spinal rod connection members 550.

Referring again to FIG. 13A, each spinal rod connection member 550 includes a body portion 552 and an extension portion 554. The body and extension portions 552, 554 define a cavity 555 therebetween that is configured to receive one of the insertion arm assembly 530 and the receiving arm assembly 510. With brief reference to FIG. 13C, spinal rod connection member 550 includes first compression slot 556a and second compression slot 556b. Spinal rod connection member 550 further includes a locking screw receptacle 558 that is configured to receive a cross member connection locking screw 580, as will be described further below. A spinal rod connection passage 560 is defined through the extension portion 554 of the spinal rod connection member 550 and is configured to receive and securely retain a spinal rod 90 as shown in FIG. 1B.

Figure 13C:
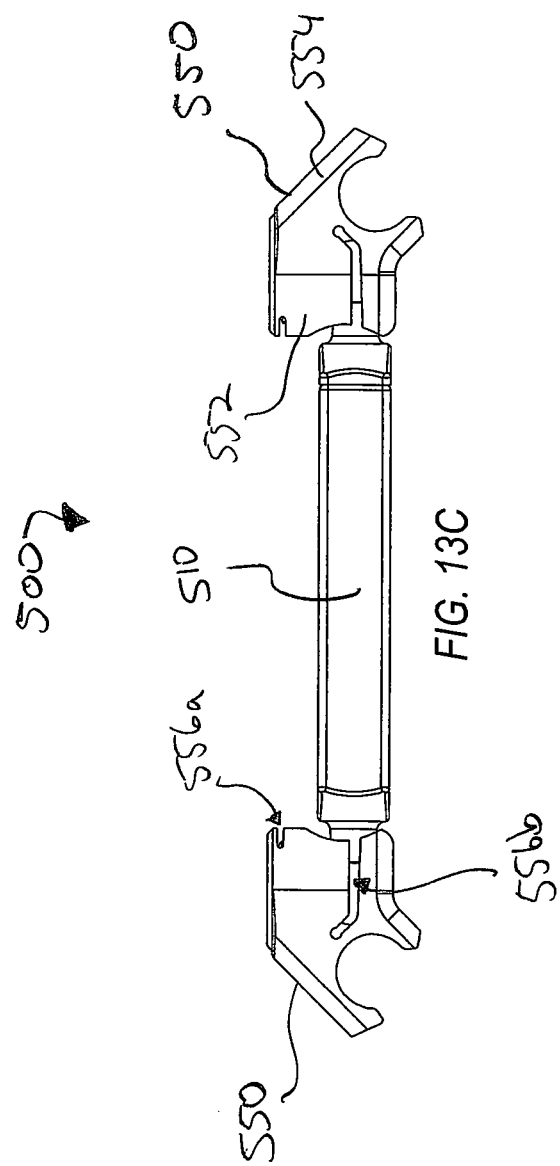
FIG. 13C is a side view of the transverse connector of FIG. 13A.
Figure 13D:
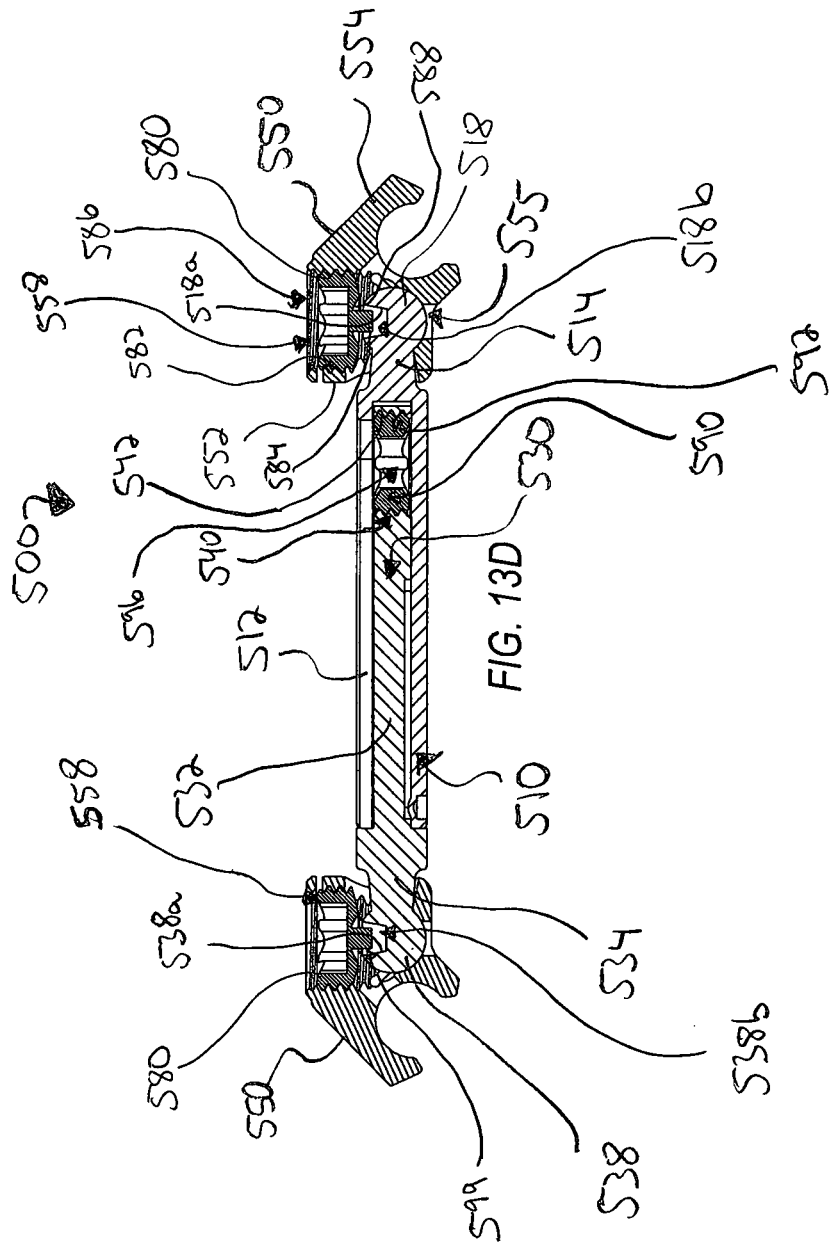
FIG. 13D is a side cross-sectional view of the transverse connector of FIG. 13A.

As best depicted in FIG. 13D, receiving arm assembly 510 includes a receiving arm 512 and a receiving arm extension 514 having an articulating ball joint 518 on a lateral end of the receiving arm extension 514. The ball joint 518 is configured to be positioned within the cavity 555 defined between the body and extension portions 552, 554 of one of the spinal rod connection members 550. Ball joint 518 includes a top surface 518a that defines a ball joint recess 518b.

Referring also to FIG. 13B, receiving arm assembly 510 further includes receiving arm guides 510a and 510b that define an opening 522 therebetween. The opening 522 is configured to receive insertion arm assembly 530.

As shown in FIG. 13D, insertion arm assembly 530 includes an insertion arm 532 and an insertion arm extension 534. The insertion arm extension 534 includes an articulating ball joint 538 on a lateral end of the insertion arm extension 534. Similar to ball joint 518, ball joint 538 includes a top surface 538a that defines a ball joint recess 538b. Insertion arm 532 includes a screw receptacle 540 having internal threads 542 defined along an inner surface of the screw receptacle 540 for receiving an insertion arm locking screw 590.

Continuing to refer to FIG. 13D, insertion arm locking screw 590 is shown having threads 592 and a tool cavity 596 so that a clinician may manually screw locking screw 590 with a suitable tool (not shown) within screw receptacle 540 of insertion arm 532.

A pair of cross member connection locking screws 580 is also shown in FIG. 13D. Each locking screw 580 is shown positioned within one of the locking screw receptacles 558 of one of the spinal rod connection members 550. Each cross member connection locking screw 580 has threads 582 defined along an external surface of the locking screw 580. On a top portion, locking screw 580 includes a tool cavity 586 so that a clinician may manually screw locking screw 580 with a suitable tool (not shown), for example, but not limited to a screwdriver or a TORX® wrench. On a bottom portion, locking screw 580 includes a concave cavity 588 and a post 584 that is provided in the center of the cavity 588. Post 584 is configured to be inserted within recess 538b of ball joint 538 or recess 518b of ball joint 518 during assembly. In particular, to provide a friction fit during assembly, as locking screw 580 is placed and rotated (e.g., screwed) into locking screw receptacle 558, concave cavity 588 and post 584 on the underside of screw 580 exerts compressive forces against ball joint 538 or ball joint 518. The compressive forces may be exerted against top surface 538a or top surface 518a. As can be appreciated, when locking screw 580 is fully seated within recess 518b or recess 538b, one or both of the spinal rod connecting members 550 may maintain a limited range of motion with respect to ball joint 518 or ball joint 538 by virtue of a space 599, which may be annular, defined between the post 584 of locking screw 580 and one of the top surfaces 518a or 538a of recess 518b, 538b.

Figure 14A:
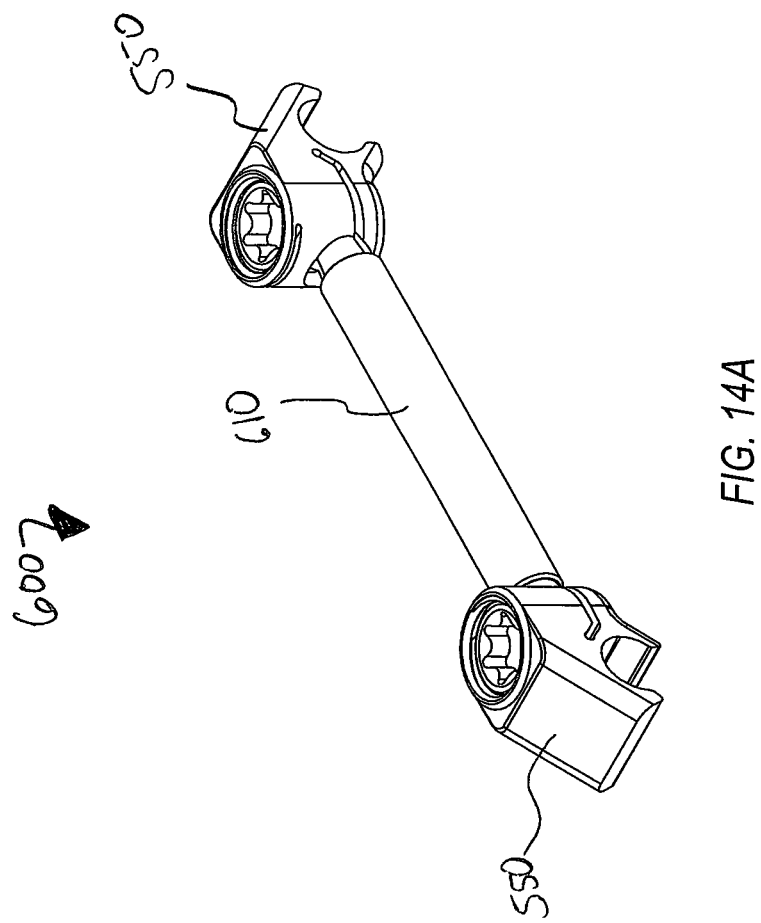
FIG. 14A is a perspective view of yet another embodiment of a transverse connector in accordance with the present disclosure.

Referring now to FIGS. 14A and 14B, another embodiment of a transverse connector is shown which is generally referred to as transverse connector 600. Transverse connector 600 is similar to other embodiments described herein and therefore is only described herein to the extent necessary to describe the differences in construction and operation thereof. Transverse connector 600 includes an arm assembly 610 disposed between a pair of substantially identical spinal rod connection members 550.

Illustrated best in FIG. 14B, arm assembly 610 includes a cross member 612 having a pair of arm extensions 614 extending from the cross member 612 on opposed lateral ends of the cross member 612. Each arm extension 614 tapers to a ball joint 618 on the lateral end of the arm extension 614. Like, ball joint 518, ball joint 618 is configured to be positioned within the cavity 555 defined between the body and extension portions 552, 554 of one of the spinal rod connection members 550. Ball joint 618 includes a top surface 618a that defines a ball joint recess 618b. As can be appreciated, one or more locking screws 580 may be used in connection with transverse connector 600 substantially similarly as described above with regard to transverse connector 500.

Figure 15A:
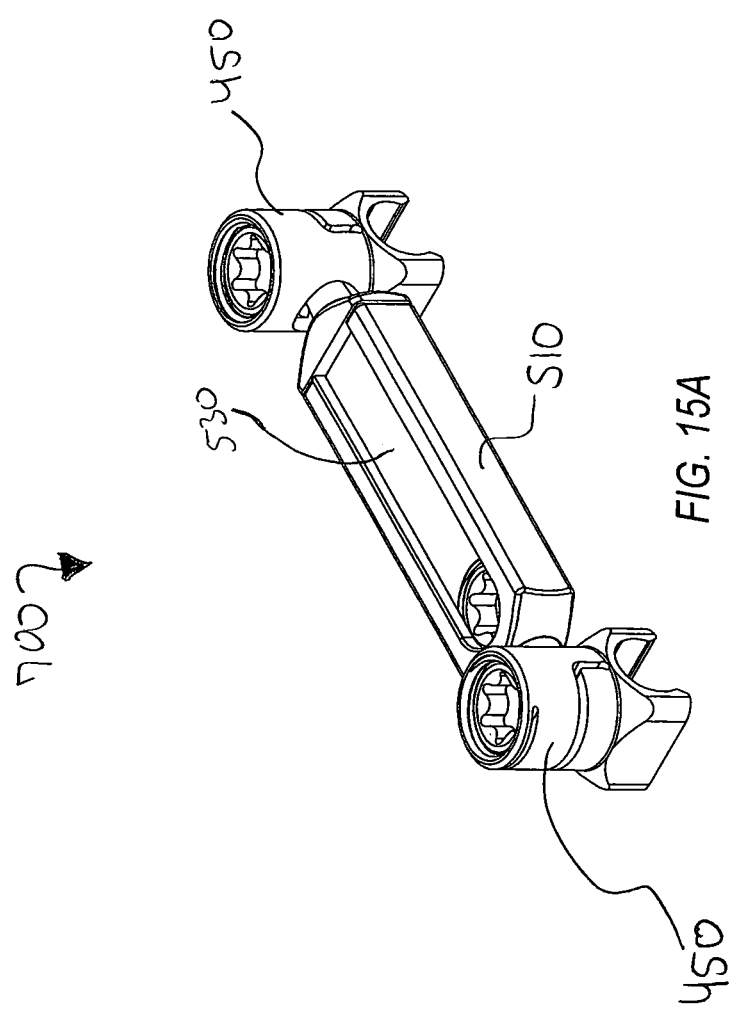
FIG. 15A is a perspective view of yet another embodiment of a transverse connector in accordance with the present disclosure.
Figure 15D:
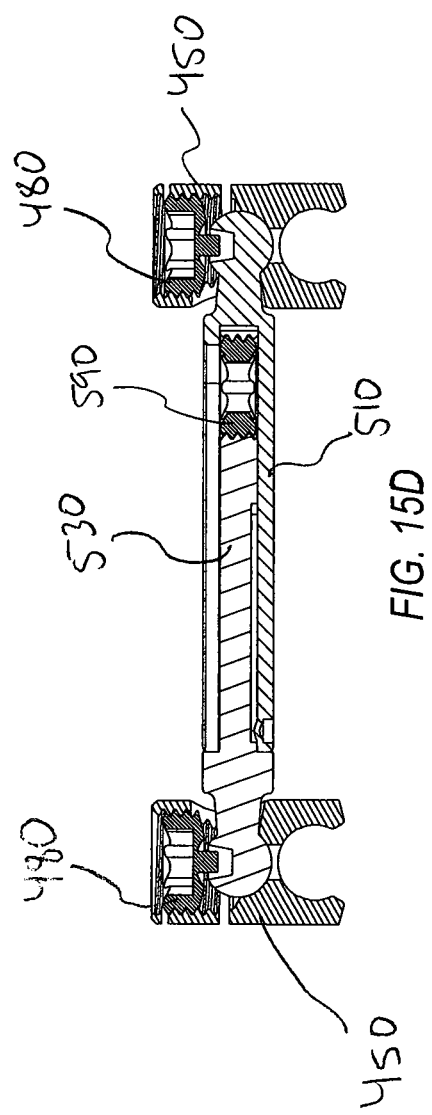
FIG. 15B is a side cross-sectional view of the transverse connector of FIG. 15A.

Turning to FIGS. 15A and 15B, yet another embodiment of a transverse connector is shown which is generally referred to as transverse connector 700. Transverse connector 700 is similar to other embodiments described herein and therefore is only described herein to the extent necessary to describe the differences in construction and operation thereof. Transverse connector 700 includes a pair of substantially identical spinal rod connection members 450, a receiving arm assembly 510, and an insertion arm assembly 530. One of the pair of spinal rod connection members 450 is secured to the receiving arm assembly 510 via locking screw 480 and the other of the pair of the spinal rod connection members 450 is secured to the insertion arm assembly 530 via another locking screw 480. The receiving arm assembly 510 and the insertion arm assembly 530 are slidably disposed relative to one another between the pair of spinal rod connection members 450. The receiving arm assembly 510 and the insertion arm assembly 530 may be fixed relative to one another via arm locking screw 590.

Figure 16:
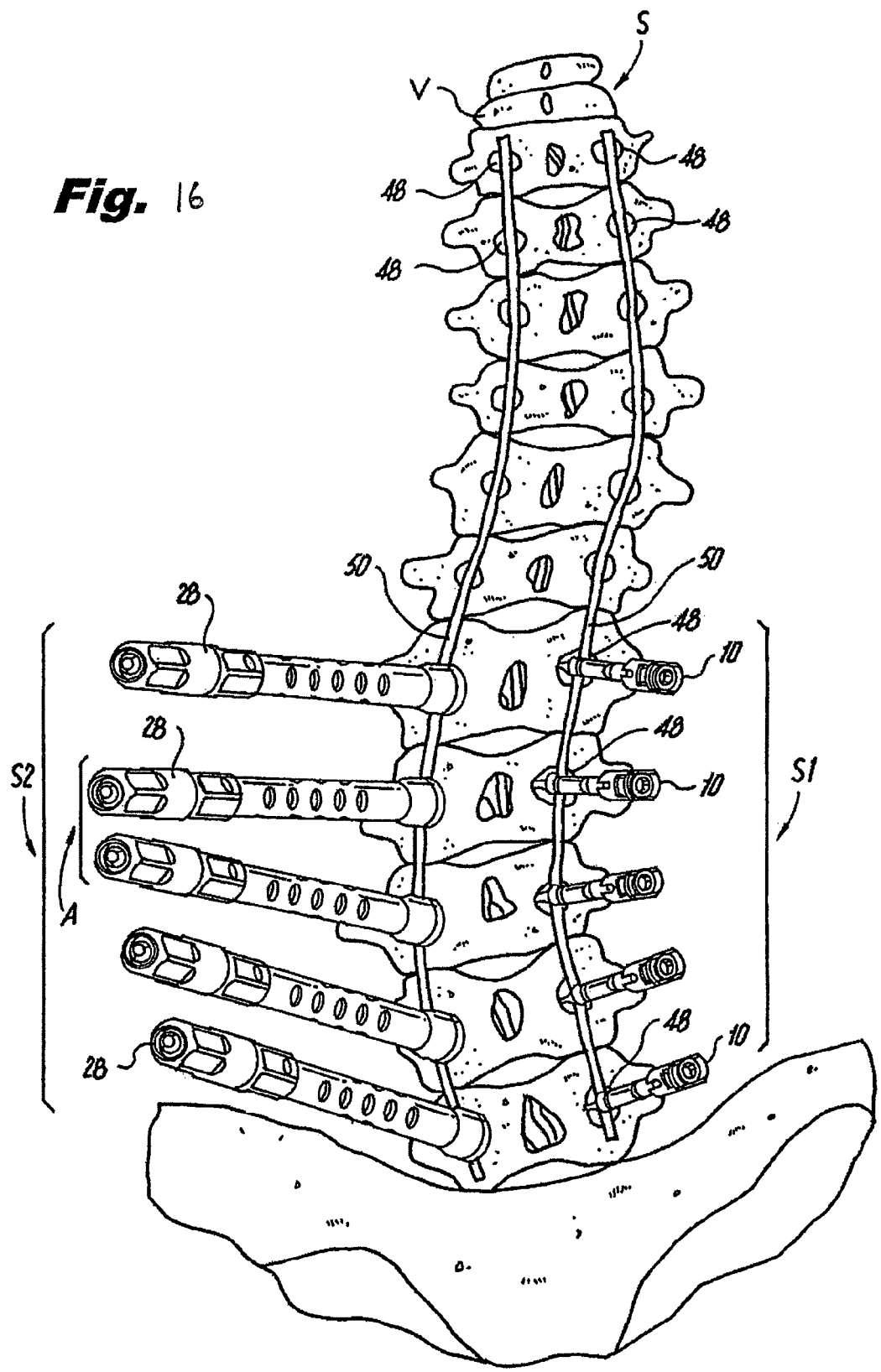
FIG. 16 shows a dorsal view of a section of a spinal column with a plurality of bone screws attached to spinal vertebrae of the spinal column, two spinal rods engaged with the plurality of bone screws, a plurality of rod reduction devices attached to the bone screws, and a plurality of manipulators attached to the bone screws.

As can be appreciated, any of the embodiments of the presently disclosed transverse connector can be used in connection with the bone screw/spinal rod construct illustrated in FIG. 16 and discussed above.

Any of the embodiments of the presently disclosed transverse connector can be manufactured as components by methods known in the art, to include, for example, molding, casting, forming or extruding, and machining processes. The components can be manufactured using materials having sufficient strength, resiliency and biocompatibility as is well known in the art for such connectors. By way of example only, suitable materials can include implant grade metallic materials, such as titanium, cobalt chromium alloys, stainless steel, or other suitable materials for this purpose. It is also conceivable that some components of the connector can be made from plastics, composite materials, and the like.

It is also within the concept of the inventors to provide a kit, which includes at least one of the embodiments of the presently disclosed transverse connector. The kit can also include additional orthopedic devices and instruments; such as for example, instruments for tightening or loosening the locking screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present disclosure to include modifications and varying configurations without departing from the scope of the disclosure that is limited only by the claims included herewith.

The invention claimed is:

1. A transverse connector system comprising:
 a first spinal rod;
 a second spinal rod;
 a cross member including a first end and a second end that opposes the first end, the cross member including a first ball joint disposed at the first end and a second ball joint disposed at the second end, the cross member defining a longitudinal axis extending through the first and second ends; and
 first and second spinal rod connecting members, the first spinal rod connecting member secured to the first ball joint and the second spinal rod connecting member secured to the second ball joint, each of the spinal rod connecting members defining a spinal rod connecting passage therethrough for reception of one of the spinal rods, each spinal rod connecting member adapted to receive a locking screw, the locking screw extending to a mating surface at a leading end thereof, the mating surface being receivable within a complementary mating surface of a respective one of the ball joints such that rotation of the locking screw advances the mating surface of the locking screw into the complementary mating surface of the respective one of the ball joints to retain a respective one of the spinal rod connecting members in a fixed relationship with the cross member,
 wherein the first spinal rod is positionable within the spinal rod connecting passage of the first spinal rod connecting member, the first spinal rod connecting member receives the locking screw such that the locking screw shares a common axis with the first ball joint and with the first spinal rod, the common axis being transverse to the longitudinal axis of the cross member,
 wherein the first spinal rod connecting member includes a first spinal rod retention lip and a second spinal rod retention lip positioned adjacent to an opening defined in a bottom most surface of the first spinal rod connecting member, the first and second spinal rod retention lips projecting toward one another to facilitate retention of the first spinal rod in the spinal rod connecting passage of the first spinal rod connecting member.

2. The transverse connector system according to claim 1, wherein each of the first and second spinal rod connecting members defines a ball joint receptacle, each ball joint receptacle having a lateral opening configured to receive one of the first and second ball joints of the cross member.

3. The transverse connector system according to claim 1, wherein the cross member includes an offset cross member providing an offset configuration such that the first and second spinal rod connecting members are disposed in a first plane and at least a portion of the offset cross member is disposed in a second plane that is spaced apart and parallel to the first plane.

4. The transverse connector system according to claim 1, wherein the cross member includes an insertion arm and a receiving arm, the receiving arm defining a space therein and being configured to receive the insertion arm to thereby adjust a length of the cross member, at least one of the insertion arm and the receiving arm having a cross member locking screw receptacle configured to receive a cross member locking screw such that rotation of the cross member locking screw exerts pressure against at least one of the insertion arm and the receiving arm to thereby maintain the insertion arm and the receiving arm in a fixed position.

5. The transverse connector system according to claim 1, wherein the complimentary mating surface of the first ball joint defines a recess and the mating surface of the locking screw includes a post that extends distally from the locking screw, the post being engagable with the recess to retain the first spinal rod connecting member in a fixed relationship with the cross member.

6. The transverse connector system according to claim 5, wherein the post and the complementary mating surface define a space therebetween to enable the first spinal rod connecting member to move relative to the first ball joint through the space such that the first spinal rod connecting member is in a fixed relationship with the cross member except for the movement through the space.

7. The transverse connector system of claim 1, wherein the common axis is perpendicular to the longitudinal axis of the cross member.

8. A transverse connector system, comprising:
a first spinal rod;
a second spinal rod; and
a transverse connector including:
   a cross member including a first end and a second end that opposes the first end, the cross member including a first ball joint disposed at the first end and a second ball joint disposed at the second end, the cross member having a first height, the first and second ball joints having a second height; and
   first and second spinal rod connecting members, the first spinal rod connecting member secured to the first ball joint and the second spinal rod connecting member secured to the second ball joint, each of the first and second spinal rod connecting members defining a spinal rod connecting passage therethrough for the reception of one of the first and second spinal rods, the spinal rod connecting passages having a third height, each spinal rod connecting member adapted to receive a locking screw, the locking screw having a mating surface that is receivable within a complementary mating surface of one of the first and second ball joints such that rotation of the locking screw retains a respective one of the spinal rod connecting members in a fixed relationship with the cross member, the first spinal rod connecting member including an opening, one of the first and second spinal rods insertable into the opening along a longitudinal axis defined by the locking screw,
   wherein each of the first, second, and third heights is offset from the other heights.

9. The transverse connector system of claim 8, wherein at least one of the first and second spinal rod connecting members is configured to articulate in multiple directions about one of the first and second ball joints of the cross member.

10. The transverse connector system of claim 8, wherein a length of the cross member is selectively adjustable.

11. A transverse connector system, comprising:
a first spinal rod;
a second spinal rod; and
a transverse connector including:
   a cross member including a first end and a second end that opposes the first end, the cross member including a first ball joint disposed at the first end and a second ball joint disposed at the second end, the cross member having a first height, the first and second ball joints having a second height; and
   first and second spinal rod connecting members, the first spinal rod connecting member secured to the first ball joint and the second spinal rod connecting member secured to the second ball joint, each of the first and second spinal rod connecting members defining a spinal rod connecting passage therethrough for the reception of one of the first and second spinal rods, the first spinal rod connecting member includes an opening having a first spinal rod retention lip and a second spinal rod retention lip to facilitate retention of one of the first and second spinal rods in the spinal rod connection passage of the first spinal rod connecting member, the spinal rod connecting passages having a third height, each spinal rod connecting member adapted to receive a locking screw, the locking screw having a mating surface that is receivable within a complementary mating surface of one of the first and second ball joints such that rotation of the locking screw retains a respective one of the spinal rod connecting members in a fixed relationship with the cross member,
   wherein each of the first, second, and third heights is offset from the other heights.

12. The transverse connector system of claim 11, wherein at least one of the first and second spinal rod connecting members is configured to articulate in multiple directions about one of the first and second ball joints of the cross member.

13. The transverse connector system of claim 11, wherein a length of the cross member is selectively adjustable.

* * * * *